United States Patent
Zhang et al.

(10) Patent No.: US 8,480,581 B2
(45) Date of Patent: Jul. 9, 2013

(54) SYSTEMS AND METHODS FOR ANEMIA DETECTION, MONITORING, AND TREATMENT

(75) Inventors: Yunlong Zhang, Mounds View, MN (US); Bin Mi, Plymouth, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 504 days.

(21) Appl. No.: 12/729,871

(22) Filed: Mar. 23, 2010

(65) Prior Publication Data

US 2010/0249865 A1 Sep. 30, 2010

Related U.S. Application Data

(60) Provisional application No. 61/162,764, filed on Mar. 24, 2009.

(51) Int. Cl.
*A61B 5/00* (2006.01)

(52) U.S. Cl.
USPC ........... 600/370; 600/322; 600/326; 600/368; 600/333

(58) Field of Classification Search
USPC .......................... 600/322, 326, 368, 370, 333
See application file for complete search history.

(56) References Cited

U.S. PATENT DOCUMENTS

| | | | |
|---|---|---|---|
| 5,277,181 A | 1/1994 | Mendelson | |
| 5,305,745 A | 4/1994 | Zacouto | |
| 6,579,498 B1 | 6/2003 | Eglise | |
| 6,709,390 B1 * | 3/2004 | Marie Pop | 600/368 |
| 7,205,701 B2 | 4/2007 | Liu | |
| 7,314,451 B2 | 1/2008 | Halperin | |
| 8,320,981 B1 * | 11/2012 | Mayer et al. | 600/310 |
| 2002/0032149 A1 * | 3/2002 | Kensey | 514/1 |
| 2002/0094515 A1 | 7/2002 | Erlach | |
| 2002/0098472 A1 | 7/2002 | Erlach | |
| 2002/0111551 A1 | 8/2002 | Erlach | |
| 2003/0036683 A1 | 2/2003 | Kehr | |
| 2004/0078219 A1 | 4/2004 | Kaylor | |
| 2004/0132675 A1 | 7/2004 | Kuo | |
| 2004/0206352 A1 * | 10/2004 | Conroy, Jr. | 128/204.23 |
| 2005/0043894 A1 | 2/2005 | Fernandez | |
| 2005/0137481 A1 * | 6/2005 | Sheard et al. | 600/508 |

(Continued)

FOREIGN PATENT DOCUMENTS

| | | |
|---|---|---|
| EP | 1394545 | 3/2004 |
| WO | WO2008066732 | 6/2008 |

OTHER PUBLICATIONS

Halvorsen, "The Effects of ACTH on Erythropoiesis in the Rabbit", Acta physiol. Scand., 1963, pp. 30-39.

(Continued)

*Primary Examiner* — Christopher D Koharski
*Assistant Examiner* — Natasha Patel
(74) *Attorney, Agent, or Firm* — Seager, Tufte & Wickhem LLC

(57) ABSTRACT

Methods and systems for implantably determining a patient's anemia status and treating anemia are described. Blood viscosity is compared one or more thresholds to determine a patient's anemia status. Therapy, in the form of electrical stimulation therapy or administration of a pharmaceutical delivered to the patient's kidneys or hypothalamus is controlled based on the anemia status.

21 Claims, 20 Drawing Sheets

U.S. PATENT DOCUMENTS

| | | | |
|---|---|---|---|
| 2006/0041280 A1* | 2/2006 | Stahmann et al. | 607/17 |
| 2006/0116720 A1 | 6/2006 | Knoblich | |
| 2006/0178841 A1 | 8/2006 | Fernandez | |
| 2007/0106333 A1 | 5/2007 | Fernandez | |
| 2007/0156179 A1 | 7/2007 | S.E. | |
| 2007/0179389 A1 | 8/2007 | Wariar | |
| 2007/0232940 A1* | 10/2007 | Fine et al. | 600/504 |
| 2007/0282172 A1 | 12/2007 | Toumazou | |
| 2008/0058630 A1 | 3/2008 | Robertson | |
| 2008/0077375 A1 | 3/2008 | Fernandez | |
| 2008/0119907 A1 | 5/2008 | Stahmann | |
| 2008/0195162 A1 | 8/2008 | Lippert et al. | |
| 2009/0025459 A1 | 1/2009 | Zhang | |
| 2009/0036948 A1 | 2/2009 | Levin | |
| 2009/0118666 A1* | 5/2009 | Blomqvist et al. | 604/66 |
| 2009/0326613 A1 | 12/2009 | Knoblich | |

OTHER PUBLICATIONS

International Search Report and Written Opinion dated Jul. 5, 2010 from PCT Application No. PCT/US2010/028434, 19 pages.

Bauters et al., "Influence of diabetes mellitus on heart failure risk and outcome", Cardiovascular Diabetology, Vo. 2:1, 2003.

Boss et al., "Blood viscosity measurement and intervention:", Pharmaceutical Visions, printed from internet Mar. 23, 2010.

Ditting et al., "Renal sympathetic nerves modulate erythropoietin plasma levels after transient hemorrhage in rats", Am J Physiolo Renal Physiol, vol. 293, Jul. 25, 2007.

Fink et al., "Erythropoietin production after renal denervation or beta-adrenergic blockade", American Journal of Physiology, vol. 230, No. 2, Feb. 1976.

Firouzian et al., "Planar Sensor Structures for Whole Blood Viscosity Measurements", printed from internet Mar. 23, 2010.

Guhr, "Monitoring Blood Coagulation with Acoustic Methods", Institute for Solid State Research, printed from internet Mar. 23, 2010.

Halvorsen, "Effects of Hypothalamic Stimulation on Erythropoiesis and on the Production of Erythropoiesis-Stimulating Factors in Intact and Nephrectomized Rabbits", Annals of the New York Academy of Sciences, vol. 149, Dec. 16, 2006.

Jacobs et al., Epidural Spinal Cord Electrical Stimulation Improves Microvascular Blood Flow in Severe Limb Ischemia, Jul. 31, 1987.

Katz, "Mechanisms and Treatment of Anemia in Chronic Heart Failure", Le Jacq Communications, Sep.-Oct. 2004.

Klabunde, "Cardiovascular Physiology Concepts", Apr. 10, 2007.

Lacombe et al., "Peritubular Cells are the Site of Erythropoietin Synthesis in the Murine Hypoxic Kidney", J. Clin. Invest;, vol. 81, Feb. 1988, pp. 620-623.

Marcus et al., "Foundations for lntegrtaive Musculoskeletal Medicine", 2005, pp. 430-440.

Medado et al., "The effect of electrical stimulation of the central nervous system on erythropoiesis in the rat. II. Localization of a specific brain structure capable of enhancing red cell production", J. Lab & Clin. Med., vol. 69(5), May 1967, pp. 776-786.

Nielson et al., "Blood Glucose and Heart Failure in Nondiabetic Patients", Diabetes Care, vol. 28, 2005. (abstract only).

Pries et al., "Blood viscosity in tube flow: dependence on diameter and hematocrit", Am J Physiol., vol. 263(6Pt2), Dec. 1992. (abstract only).

Schulte et al., "Cortical electrical stimulation alters erythrocyte perfusion pattern in the cerebral capillary network of the rat", Brain Research, vol. 963, 2003, pp. 81-92.

Segal et al., "The Effect of Electrical Stimulation of the Hypothalamus on Red Cell Production and Destruction in the Rat", Israel J. Med. Sci., vol. 7, 1971, pp. 1017-1024.

Segal et al., "Augmented Red Cell Sequestration After Prolonged Electrical Stimulation of the Posterior Hypothalamus in Rats", Journal of Reticuloendothelial Society, vol. 9, 1971, pp. 225-236.

* cited by examiner

SYSTEMS AND METHODS FOR ANEMIA DETECTION, MONITORING, AND TREATMENT

RELATED APPLICATIONS

This application claims the benefit of Provisional Patent Application Ser. No. 61/162,764, filed on Mar. 24, 2009, to which priority is claimed pursuant to 35 U.S.C. §119(e) and which is hereby incorporated herein by reference.

FIELD OF THE INVENTION

The present invention relates generally to detection and treatment of anemia.

BACKGROUND

Anemia is a blood disorder that occurs when the total volume of red blood cells and/or the amount of hemoglobin in the red blood cells is reduced below normal values. Anemia causes symptoms such as general fatigue, weakness, interrupted concentration, and shortness of breath. Heart failure (HF) is a common comorbidity with anemia. Very severe anemia prompts the body to attempt to increase cardiac output which may lead to heart failure. On the other hand, severe heart failure leads to heart failure decompensation which produces a fluid overload in the blood, causing an increase in plasma without a corresponding increase in red blood cells, which in turn results in anemia.

Anemia is often treated by pharmaceuticals, for example, by administering an iron supplement, vitamin B12, folic acid, recombinant erythropoietin, and/or erythropoiesis-stimulating agents such as epoetin and/or darbepoetin. Erythropoiesis-stimulating agents ultimately stimulate an increase the production of red blood cells. Although administration of erythropoiesis-stimulating agents and/or other pharmaceuticals is beneficial to treat anemia and may concurrently improve heart failure symptoms, such treatments can increase the risk of thromboembolism. Other treatments for severe anemia include blood transfusions which also pose risks to the patient.

Anemia is most commonly detected by performing patient-external blood tests that include measuring hemoglobin (the iron-carrying part of red blood cells), or by determining hematocrit (the volume of red blood cells in a specified amount of blood). Anemia assessments are usually carried out in clinical settings, therefore days or weeks may elapse between tests. The lapse of time between tests hinders the timely delivery of therapy.

For the reasons stated above, and for other reasons stated below which will become apparent to those skilled in the art upon reading the present specification, there is a need in the art for methods and systems that provide improved approaches for detecting and treating anemia, particularly for patients with heart failure. The present invention fulfills these and other needs and provides for other improvements over the prior art.

SUMMARY

The present invention is directed to systems and methods for detecting and treating anemia. One embodiment involves a method of operating an implantable medical system. Blood viscosity is sensed using a sensor configured for implantation within a blood vessel or heart. The blood viscosity is compared to one or more thresholds respectively associated with one or more hematocrit levels. An anemia status of a patient is determined based on comparison of the blood viscosity to the one or more thresholds. An electrical stimulation delivered to one or both kidneys or a hypothalamus of the patient is controlled based at least in part on the anemia status.

According to some implementations, the anemia status may be trended over time and stored. A rate of increase or decrease in the anemia status may be used to control the electrical stimulation therapy.

The blood viscosity may be temperature-compensated using sensed blood temperature.

The progression or regression of heart failure can be assessed based on the anemia status trend. Heart failure therapy may be modified based on the anemia status trend.

Hemodilutional anemia may be detected based on the anemia status trend. An onset of a heart failure decompensation event may be detected based on the detection of hemodilutional anemia.

Thoracic impedance may be sensed. The thoracic impedance may be used together with anemia status to detect an onset of a heart failure decompensation event.

The electrical stimulation therapy may be controlled based in part on an evaluation of thromboembolism risk.

The electrical stimulation may use a signal having a frequency between about 0.1 Hz and about 10 kHz and/or producing an electric field strength of about 0.1 V/cm and about 10 V/cm volts per centimeter.

Another embodiment of the invention is directed to a medical system for determining anemia status. An implantable sensor senses blood viscosity and generates a signal modulated by the blood viscosity. Implantable circuitry receives the blood viscosity signal and stores the blood viscosity. An anemia module compares the blood viscosity to one or more thresholds associated with hematocrit and determines an anemia status of a patient based on the comparison. The anemia module may also develop and store a trend of the anemia status over time.

The system may include a heart failure diagnostics module configured to detect an onset of heart failure decompensation based on the anemia status trend.

According to some implementations, the implantable circuitry and the anemia module are incorporated in an implantable cardiac therapy device that includes a cardiac therapy controller configured to control a cardiac pacing therapy based on the anemia status trend.

The anemia module may be configured to generate an alert signal based on the anemia status trend.

The anemia module may evaluate thromboembolism risk and generate an alert signal based on the thromboembolism risk.

A further embodiment is directed to an implantable medical system for treating anemia. The medical system includes an implantable sensor configured to generate a signal modulated by blood viscosity. An anemia module compares the blood viscosity to one or more thresholds respectively associated with one or more hematocrit levels and determine an anemia status of a patient based on the comparison. A therapy module delivers therapy to the patient based on the anemia status or blood viscosity.

In some configurations, the anemia module is configured to evaluate thromboembolism risk and the therapy module is configured to deliver therapy to the patient based on the thromboembolism risk.

The therapy module may include a drug pump or an electrical stimulator configured to deliver electrical stimulation therapy to one or both kidneys or to the hypothalamus. The therapy module may also be configured to provide cardiac resynchronization pacing for heart failure.

The anemia module may be configured to detect onset of heart failure decompensation based on the anemia status and to generate an alert signal in response to detection of the onset of heart failure decompensation.

The anemia module may be configured to generate an alert signal based on the anemia status.

The blood viscosity sensor may be an acoustic sensor.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
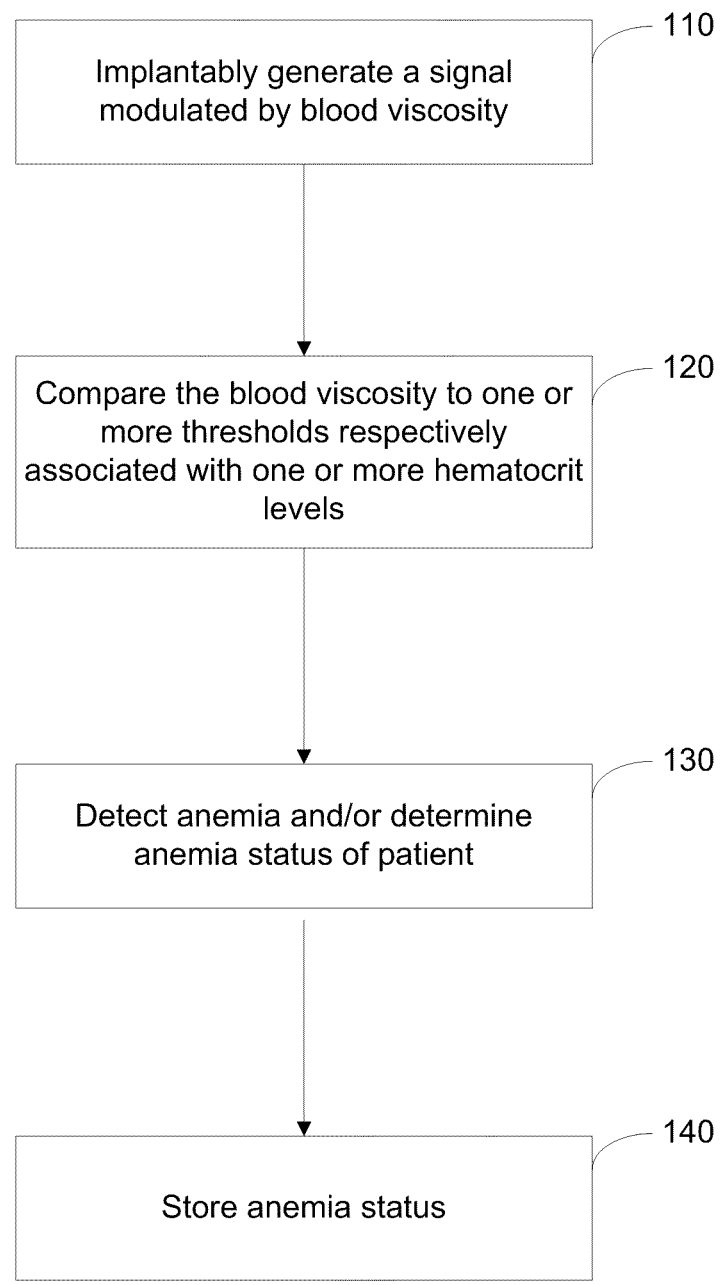
FIG. 1A is a flow diagram illustrating a method of detecting anemia and/or determining a patient's anemia status based on the output of a blood viscosity sensor.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments that can be used to practice the invention. It is to be understood that other embodiments are possible, and structural and functional changes may be made to the illustrated embodiments without departing from the scope of the present invention.

Systems, devices or methods according to the present invention may include one or more of the features, structures, methods, or combinations thereof described herein. For example, a device or system may be implemented to include only one or any number of the advantageous features and/or processes described. It is intended that such device or system need not include all of the features described herein, but may be implemented to include selected features that provide for useful structures and/or functionality. Such a device or system may be implemented to provide a variety of therapeutic and/or diagnostic functions.

The prevalence of anemia ranges as high as 50% in patients with severe heart failure. Anemia has been shown to be a significant predictor of hospitalization among these patients who face a 3% increase in risk of death for every 1% decline in hematocrit. Embodiments of the invention are directed to systems and methods for detecting anemia, monitoring anemia status, and/or treating anemia. These embodiments are particularly useful for patients who concurrently suffer from heart failure.

Red blood cells include hemoglobin, an iron containing oxygen transport metalloprotein, which provides a mechanism for delivering oxygen to the body tissues. Anemia involves a reduced amount of hemoglobin in the blood, which may occur through either decreased red blood cell volume or a decrease in the oxygen-carrying capability of the red blood cells. Hemoglobin is a common method for assessing anemia. The normal value of hemoglobin varies with age and gender. Normal values of hemoglobin are greater than about 13-18 gm/dL for males and greater than about 12-16 gm/dL in females. Hematocrit is also a useful measure for assessing anemia as it provides the proportion of blood volume occupied by red blood cells. When the proportion of red blood cells in a volume of blood (hematocrit) is reduced, the oxygen carrying capacity of the volume of blood is correspondingly reduced. If the reduction is significant enough, the patient becomes anemic. Normal values of hematocrit are greater than about 45+/−7% in males and greater than about 42+/−5% in females; normal values of red blood count are greater than about 5-6 million/mm$^2$ for males and greater than about 4-5 million/mm$^2$ for females; normal values of hemoglobin concentration are greater than about 13 g/dl for males and greater than about 12 g/dl for females. Blood parameter values below these normal threshold values can indicate anemia.

Some embodiments of the invention are directed to monitoring and reporting anemia status. One or more blood parameters are monitored and are used to detect anemia and/or determine the patient's anemia status. The blood parameters can be directly sensed parameters such as blood viscosity, blood impedance and/or blood temperature. Additionally or alternatively, the blood parameters can be derived from the directly sensed blood parameters. For example, hematocrit is a blood parameter which can be derived from sensed blood viscosity or blood impedance; hemoglobin concentration and red blood cell count are blood parameters that can be derived from laser scattering and/or other optical measurements.

One or more blood parameters may be sensed using one or more fully or partially implantable sensors and/or one or more patient-external sensors. For example, blood parameters may be measured via optical techniques using a patient-external sensor module. The external sensor module may be coupled through a wire or wirelessly to a patient interface device. The patient interface may link to an implantable medical (therapy or diagnostic) device and/or to a patient-external device such as an advanced patient management (APM) server. The patient interface may be located at the patient's bedside, and/or may be carried by the patient throughout the day to facilitate ease and frequency with which measurements can be taken. The interface may include a screen, a speaker and/or a vibratory element that can be used to remind the patient when a blood parameter measurement is scheduled to be taken, such as by an audible, visual, or vibratory alert. In some configurations, the patient-external sensor module may be attached to the patient, e.g., an adhesive-backed sensor module, and optical measurements may be used to determine blood parameters such as hemoglobin and hematocrit. Implantable and/or patient-external sensors may be used to collect blood parameter information automatically and/or on command by the patient and/or the patient's health car provider through the APM server, for example.

Some embodiments rely on the relationship between blood viscosity or blood impedance and hematocrit level to detect anemia and/or quantify the patient's anemia status. In general, for a given temperature, both blood viscosity and blood impedance increase with hematocrit level. However, variations of blood viscosity and impedance with temperature are typically present and may obscure an accurate measurement of hematocrit. Appropriate corrections for temperature variations may be made if blood temperature is known.

In some embodiments, anemia may be detected based on the comparison of a blood parameter value and a threshold value. For example, a medical device may compare a current blood parameter value to a predetermined threshold which has been programmed into the device. If the blood parameter value is below the threshold (or above the threshold if the threshold represents a maximum acceptable value) then the patient is declared to be anemic. In some embodiments, a baseline threshold may be initially determined from blood parameter measurements taken for the patient over a period of time prior to determining the patient's anemia status or detecting anemia. After the baseline threshold is initially determined, a subsequent blood parameter value is compared to the baseline threshold. In some embodiments, the rate of change of the blood parameter may be compared to a rate of change threshold and if the rate of change of the blood parameter exceeds the rate of change threshold then anemia is declared.

The flow graph of FIG. 1A illustrates a method of detecting anemia and/or determining a patient's anemia status based on the output of an implantable blood viscosity sensor. Blood viscosity can be sensed, for example, using a sensor implanted within a large blood vessel, e.g., inferior vena cava, superior vena cava, or within a heart chamber, e.g., right ventricle. The sensor generates 110 a signal modulated by blood viscosity. The blood viscosity signal may be used as surrogate for hematocrit, a parameter indicative of anemia status.

The blood viscosity is compared 120 with one or more thresholds respectively associated with one or more hematocrit levels. The anemia status of the patient is determined 130 based on the comparison of the blood viscosity to the thresholds. For example, the measured blood viscosity may be compared to one or more thresholds associated with hematocrit ranges and the anemia status determined based on which range the measured blood viscosity falls within. If the blood viscosity falls below a threshold associated with a predetermined value of hematocrit, such as below a normal value of hematocrit, anemia is detected. Information associated with the patient's anemia status may be stored. For example, the information stored 140 may include the anemia status, e.g., the range associated with the blood viscosity measurement, the date and time the measurement used to determine the anemia status was taken, and/or whether anemia was detected. A trend of anemia status, hematocrit value and/or blood viscosity vs. time, may be developed.

Figure 1B:
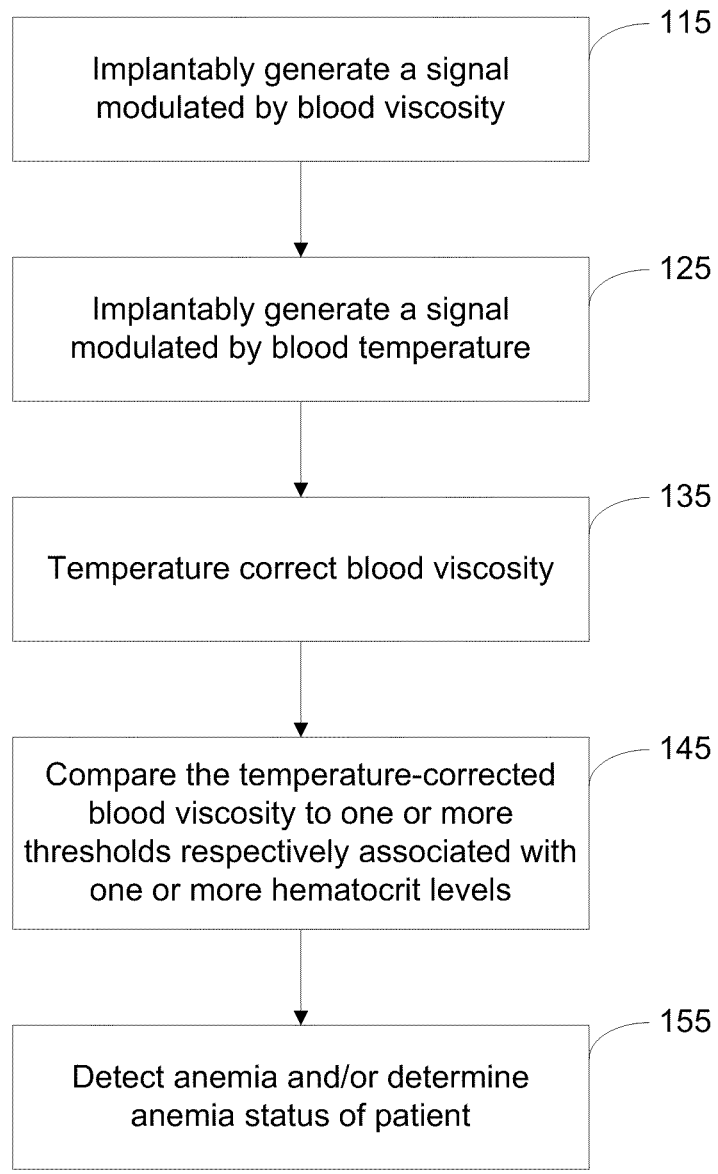
FIG. 1B is a flow diagram illustrating a method of determining anemia status and/or detecting anemia using a process that includes temperature correction of the blood viscosity.

Blood viscosity varies with blood temperature. In some implementations, illustrated by the flow diagram of FIG. 1B, determination of anemia status and/or detection of anemia are performed using a process that includes temperature correction of the blood viscosity. For example, blood viscosity and blood temperature signals are generated 115, 125 by implantable sensors. The blood viscosity is corrected 135 for variations in temperature using the blood temperature signal. The temperature-corrected blood viscosity is compared 145 to one or more thresholds associated with hematocrit levels and the patient's anemia status is determined 155 based on the comparison. Anemia may be detected if the temperature-corrected blood viscosity falls below a threshold associated with a normal hematocrit value.

Figure 1C:
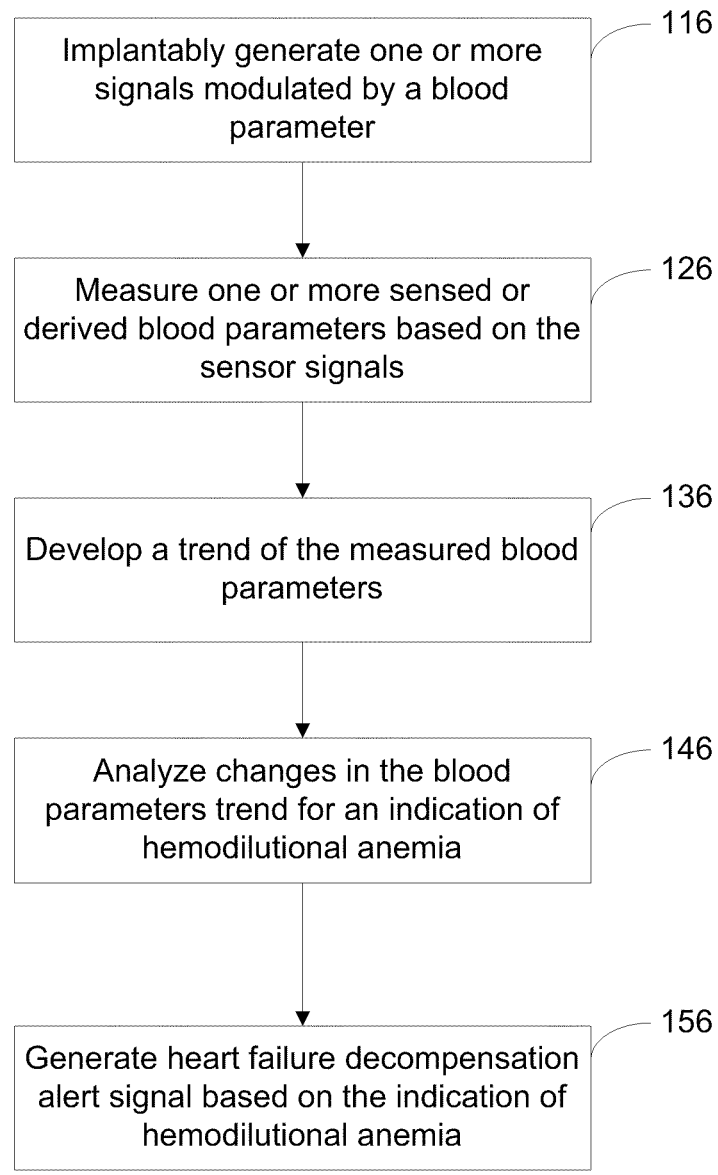
FIG. 1C is a flow diagram illustrating a process for providing early warning for heart failure decompensation based on evidence of hemodilutional anemia.

Heart failure decompensation causes an expansion of blood plasma that dilutes the proportion of red blood cells in the blood and reduces the hematocrit value, a condition referred to as hemodilutional anemia. In some embodiments, as illustrated by the flow diagram of FIG. 1C, evidence of hemodilutional anemia may be used to provide an early warning for heart failure decompensation 156. In these embodiments, one or more sensors generate 116 one or more signals indicative of one or more blood parameters. The sensed blood parameters, or blood parameters derived therefrom, are measured 126 based on the sensor signals. The sensed and/or derived blood parameters are trended 136 over a period of time. Rapid changes in the blood parameters may indicate a sudden expansion of plasma volume in the blood which results in hemodilutional anemia. The blood parameter trends are analyzed 146 for evidence of an onset of hemodilutional anemia. For example, hemodilutional anemia may be indicated if the measured blood viscosity (or the hematocrit value derived from the measured blood viscosity) decreases by a predetermined amount since a previous measurement or the decrease exceeds a predetermined rate. An alert signal is generated 156 indicating the possible onset of heart failure decompensation based on the detected changes in the blood parameters. The alert signal may involve transmitting a message to the patient and/or the patient's health care provider, such as via a text message or email.

In some embodiments, a multi-sensor approach may be used to detect or predict a heart failure decompensation event. Heart failure decompensation is generally accompanied by edema, a build up of fluid within the body tissues. Edema may be monitored in various ways, including thoracic impedance measurements, weight measurements, and/or by patient input. In some embodiments, early warning for a decompensation event is based on indications of hemodilutional anemia along with changes in the edema status of the patient.

In some embodiments, a multi-threshold approach is used. A blood parameter measurement or blood parameter trend (blood viscosity, blood impedance, derived hematocrit, etc.) is compared to a predetermined anemia threshold. An edema parameter obtained by thoracic impedance, body weight, or patient input, for example, is compared to a predetermined edema threshold. An onset of heart failure decompensation is detected based on both of these comparisons. The alert may be a multilevel alert. For example, if just one parameter falls below a threshold, then a lower priority warning alert is provided. If both parameters fall below the threshold then a higher priority alert is provided.

In some embodiments, only a single threshold is used wherein a first parameter is compared to the threshold and a second parameter is used to adjust the threshold. Adjustment of the threshold by the second parameter can be used to appropriately increase the sensitivity of the detection of heart failure decompensation. For example, consider the scenario where blood viscosity is compared to a blood viscosity threshold and edema level is used to adjust the blood viscosity threshold. An increase in the level of edema raises the blood viscosity threshold thereby reducing the decrease in blood viscosity required to generate an alert. In other words, the edema measurement adjusts the blood viscosity threshold in the direction that makes it more sensitive. A decrease in the edema level would lower the blood viscosity threshold thereby increasing the amount the blood viscosity would have to drop to trigger an alert.

Figure 2A:
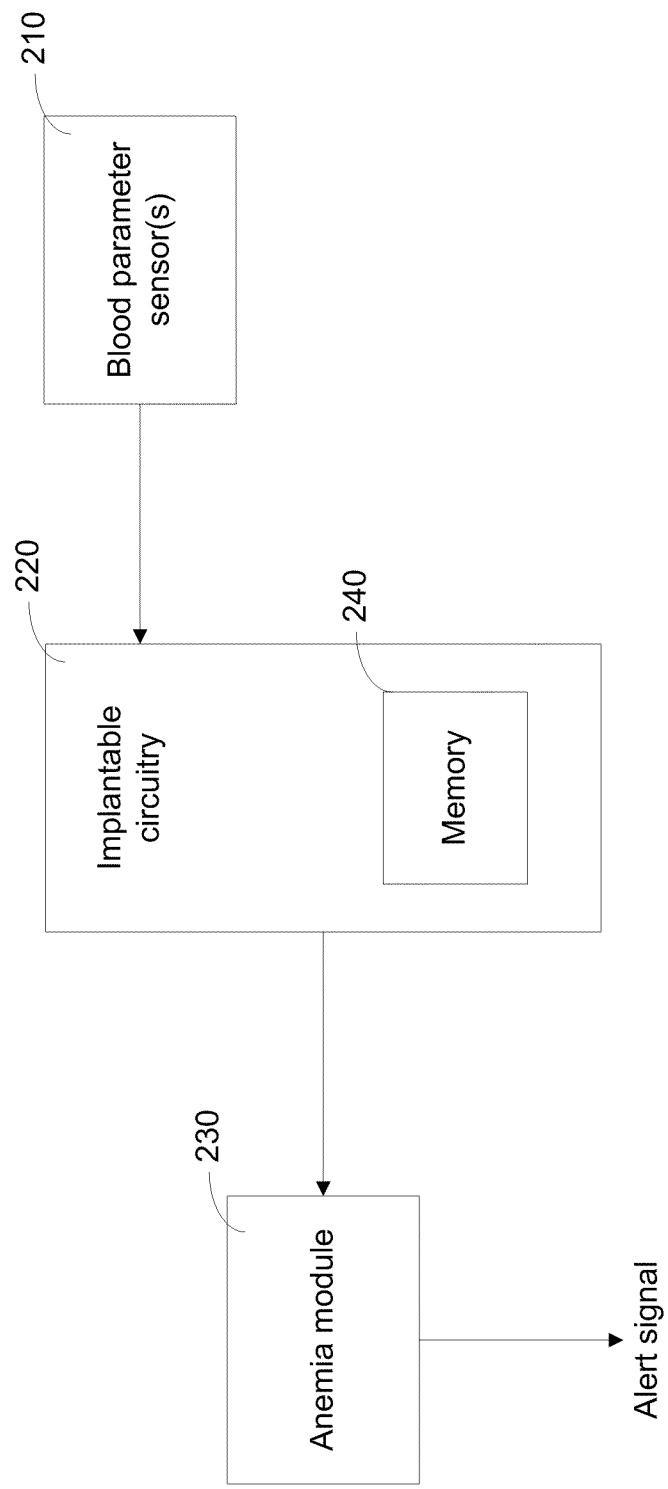
FIG. 2A is a block diagram illustrating a medical system that can be used to detect and/or monitor anemia status.

FIG. 2A is a block diagram illustrating a medical system that can be used to detect and/or monitor anemia status. In this particular embodiment, a blood parameter sensor 210 senses a blood parameter and generates a signal modulated by the blood parameter. Implantable circuitry 220 is configured to receive the blood parameter signal and may store information derived from the blood parameter signal in memory 240. The memory 240 may store one or more thresholds used for anemia detection. The memory 240 may also store an anemia status trend or other information related to anemia.

An anemia module 230 can be configured to accomplish one or more of a number of optional functions, including, for example, calculating a parameter derived from the blood parameter signal, calculating a baseline value of the blood parameter signal or a parameter derived from the blood parameter signal, calculating an average daily, weekly, and/or monthly value of the sensed or derived blood parameter, comparing the sensed or derived blood parameter to a baseline and/or to one or more thresholds to detect anemia and/or to determine anemia status, and/or developing a trend of the sensed or derived blood parameter over time.

Based on the anemia status, the anemia module may generate an alert signal indicating detection of anemia and/or a change in anemia status and/or detection of heart failure decompensation. The implantable circuitry, the anemia module, or both, may be incorporated within the housing of an implantable cardiac therapy or monitoring device, such as a cardiac monitor, pacemaker, defibrillator, or cardiac resynchronization therapy device. In some embodiments the anemia module 230 is patient-external and communicates wirelessly with the implantable circuitry 220.

As previously discussed, pharmaceuticals including erythropoiesis-stimulating agents are used to treat anemia, although these drugs can increase the risk of thromboembolism. Thromboembolism risk increases with blood viscosity. In certain embodiments, the anemia module 230 may evaluate thromboembolism risk, e.g., by comparing the blood viscosity to one or more thresholds respectively associated with levels of thromboembolism risks. Information related to the patient's thromboembolism risk may be stored and/or trended according to a method similar to that described herein for anemia status. Furthermore, if the blood viscosity exceeds a threshold associated with a predetermined maximum acceptable thromboembolism risk, then the anemia module 230 may issue a thromboembolism alert which can be distinguished from other alerts provided by the anemia module 230.

Figure 2B:
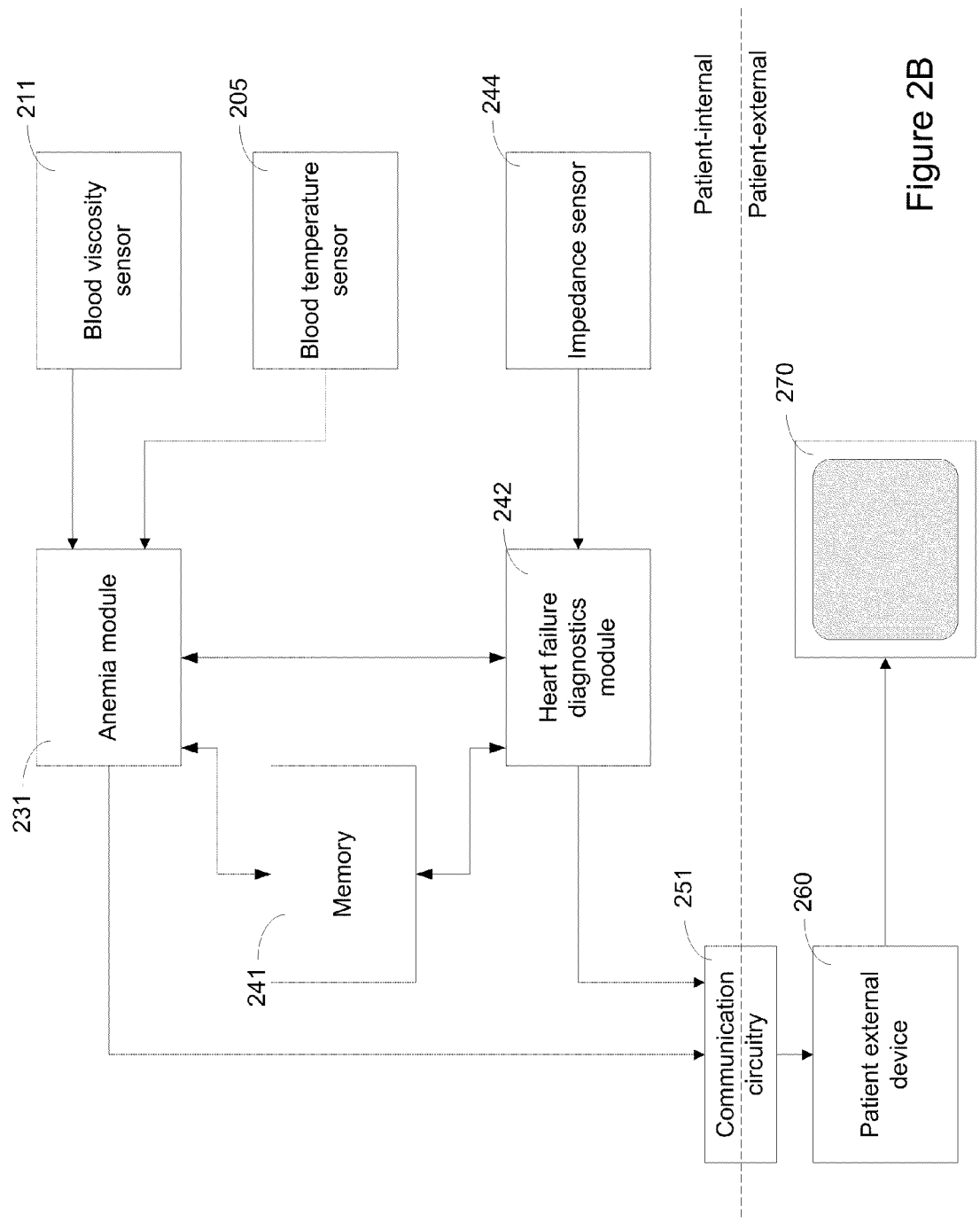
FIG. 2B is a block diagram of a medical system that provides anemia and heart failure monitoring.

FIG. 2B is a block diagram of a medical system that provides anemia and heart failure monitoring. As indicated in FIG. 2B, a first portion of the medical system includes patient-internal components implanted within the body of a patient and a second portion is patient-external. The patient-internal portion includes a blood viscosity sensor 211 and optionally includes a blood temperature sensor 205. The viscosity and temperature sensors 211, 205 are configured to be implanted within a blood vessel or heart chamber. The blood viscosity sensor 211 generates a signal modulated by blood viscosity which is received by the anemia module 231. A blood temperature signal generated by the blood temperature sensor 205 is used by the anemia module 231 to measure the blood temperature and/or to temperature correct the blood viscosity or a parameter, such as hematocrit, which is derived from the blood viscosity signal.

The anemia module 231 compares the temperature-corrected blood viscosity or hematocrit to a baseline or to one or more thresholds to detect anemia or determine the anemia status of the patient and/or to determine the risk of thromboembolism. For example, one process implemented by the anemia module 231 to detect anemia and/or determine anemia status includes comparing the blood viscosity or a parameter value derived from the blood viscosity signal to one or more programmable thresholds. Another process involves the use of a baseline value that is developed for a particular patient based on previous measurements of the blood viscosity or hematocrit. The baseline may be established by computing a central tendency, e.g., average value, median value, filtered value, etc. of a series of blood viscosity values measured over a desired time interval, e.g., one week or one month. The blood viscosity is then compared to the baseline to detect changes in anemia status.

For example, in one scenario, when the blood viscosity falls below the baseline blood viscosity by at least an offset threshold value, then anemia is declared to be present. In one example, the offset value is a fixed or programmable percentage of the baseline blood viscosity (e.g., 5%, 10%, 20%, etc.). The offset value is typically set to prevent normal physiological variations in blood viscosity from triggering anemia detection. In another example, by choosing a different threshold value, the comparison predicts that anemia is likely to occur (e.g., if the blood viscosity falls at least 10% below its baseline value, then future anemia is predicted; if the blood viscosity then falls at least 20% below its baseline value, then present anemia is declared). If anemia is predicted or declared present, that information may be telemetered or otherwise communicated to the patient's health care provider via the communication circuitry 251.

In another scenario, a thromboembolism alert may be generated if the patient's blood viscosity rises above a programmable threshold level or above a previously determined baseline blood viscosity by at least a thromboembolism offset value associated with a maximum thromboembolism risk. In a similar manner to the anemia detection process described above, the thromboembolism offset value may be a fixed or programmable percentage of the baseline blood viscosity (e.g., 5%, 10%, 20%, etc.) An alert for thromboembolism is particularly advantageous when the patient is taking drugs which combat anemia but increase the thromboembolism risk.

The patient's anemia status and/or information about blood viscosity and/or detected anemia events may be stored in memory 241. For example, the anemia module may develop a trend of the anemia status information stored in memory. Deviations from the trend may indicate worsening or improvement of the anemia status. The anemia module 231 may communicate via communication circuitry 251 with a patient-external device 260. The external device 260 may comprise circuitry ranging from a simple alert to a device programmer to an advanced patient management server configured to store and manage patient information and/or control one or more therapy devices.

The medical device may optionally include a heart failure diagnostics module 242. In one implementation, heart failure status may be determined by the heart failure diagnostics module 242 based at least in part on the information received from the anemia module 231. For example, heart failure decompensation may be indicated based on changes in the patient's anemia status. In some configurations, the heart failure status may be determined based on evidence of edema (as indicated using thoracic impedance) and/or on anemia status (as indicated by blood viscosity and/or hematocrit level). As discussed above, heart failure decompensation is often accompanied by edema, which is an increase in the fluid present within the body including within the thoracic cavity. Measurements of thoracic impedance may be used to detect edema and/or to measure an amount of fluid buildup in the thorax. The heart failure diagnostics 242 module may determine heart failure status, monitor the progression or regression of heart failure, and/or detect heart failure decompensation based on the anemia status and/or thoracic fluid measurement.

Either the anemia module 231, the heart failure diagnostics module 242, or both, are coupled via communication circuitry 251 to a patient external device 260. In one configuration, the anemia module 231 and/or the heart failure module 242 may generate an alert which is delivered to the patient or healthcare provided via the patient-external device 260. For example, the alert may take the form of an audible or visual alert, a text message or email. Information about the patient's anemia and/or heart failure status may be communicated to the patient external device 260 and may be graphically or textually displayed via a monitor 270.

In one example, the alert communication takes place the next time that the implantable medical device is interrogated by a programmer or other external device 260. In another example, the implantable medical device itself initiates a telemetric communication of the alert information to the external device 260. In yet a further example, an anemia warning is provided to the patient by the implantable medical device, for example, in the form of a sound or vibration that is perceptible by the patient.

Figure 3A:
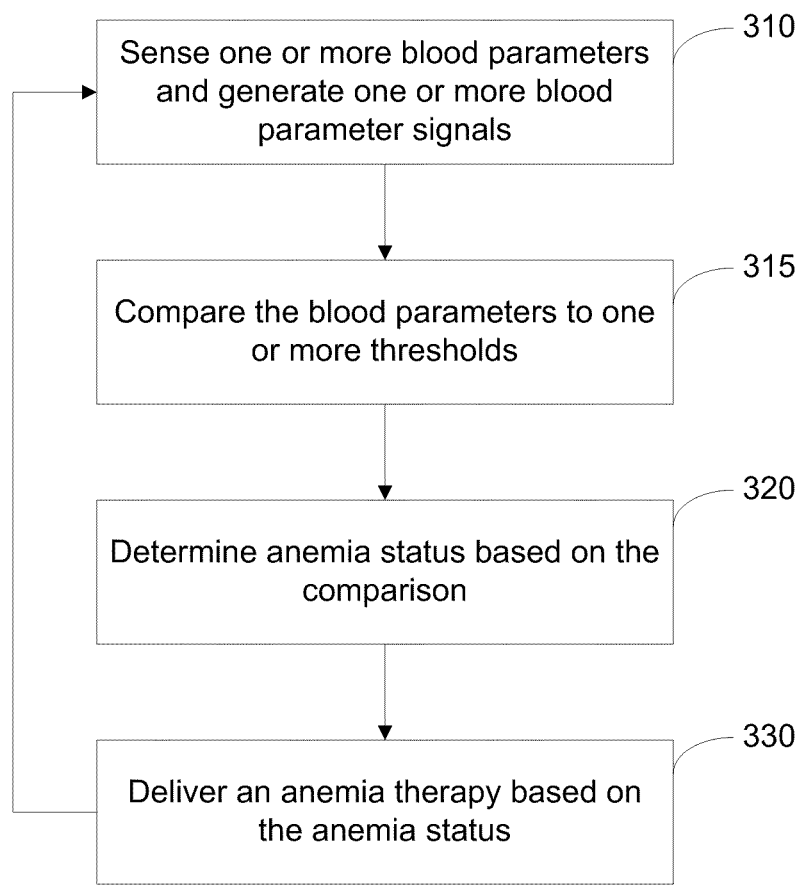
FIG. 3A is a flow diagram illustrating a process for anemia treatment in accordance with embodiments of the invention.

Some embodiments of the invention are directed to systems and methods for treating anemia such as by delivering a drug to the patient or electrically stimulating one or more body structures. FIG. 3A is a flow diagram illustrating a process for anemia treatment in accordance with embodiments of the invention. One or more blood parameters are sensed 310 and sensor signals modulated by the blood parameters are generated. According to some implementations, sensing the blood parameters may be accomplished using an implantable sensor. In other implementations, the blood parameters may be sensed using a patient-external sensor. In yet other implementations, both implantable and patient-external sensors may be used.

The blood parameters are compared 315 to one or more thresholds. Anemia status is determined 320 based on comparison of the blood parameter to the one or more thresholds. Anemia may be detected if the comparison indicates that one or more of the blood parameters falls below a threshold (or above the threshold depending on the threshold and parameter). An anemia therapy is delivered 330 based on the anemia status. The anemia status may optionally be stored and/or a trend of anemia status over time may be developed and stored. In some embodiments, the processes 310-330 are performed in a continuous loop, with the blood parameter signal used to develop a feedback signal to control the anemia therapy.

Figure 3B:
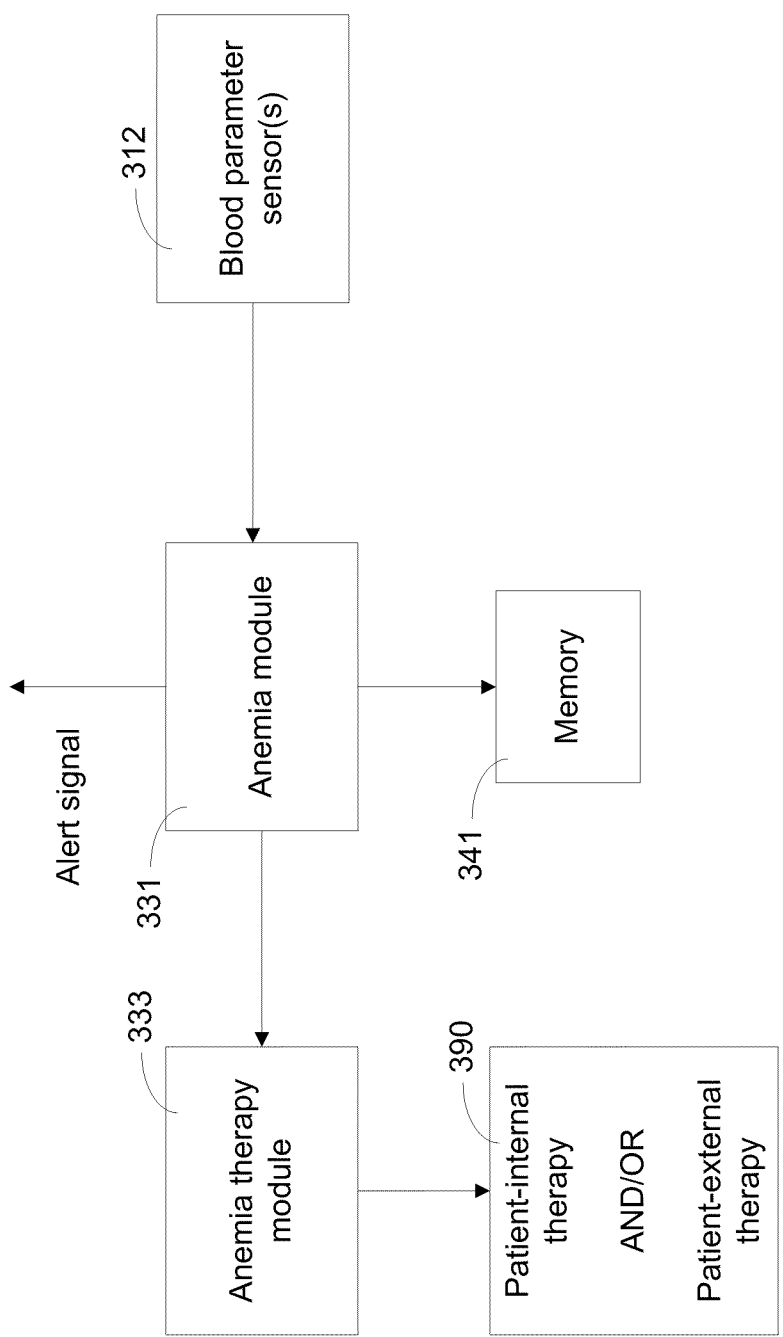
FIG. 3B is a block diagram of a medical system capable of providing both anemia monitoring and anemia treatment.

FIG. 3B is a block diagram of a medical system capable of providing both anemia monitoring and anemia treatment. A blood parameter sensor 312 generates a signal modulated by a physiological parameter related to anemia. An anemia module 331 receives the blood parameter signal and compares the blood parameter to threshold or baseline values to detect anemia and/or to determine the patient's anemia status. The anemia status may be trended over a period of time and stored in memory. 341. If anemia is detected or if the anemia status of the patient deteriorates, the anemia module 331 generates an alert to notify the patient and/or the patient's health care provider.

In addition to the anemia monitoring functions described above, the medical system of FIG. 3B has the capability of delivering therapy to treat anemia. The medical system includes an anemia therapy module 333 which controls the operation of a patient internal and/or a patient external therapy delivery module 390.

For example, in some configurations, the anemia therapy comprises electrical stimulation of body structures, such as one or both kidneys, the central nervous system, the spinal cord, or brain, to increase red blood cell production. For example, the kidneys are a major source of erythropoietin (EPO) production which is a hormone that stimulates the bone marrow to produce red blood cells. It is believed that electrical stimulation of kidney structures (such as the kidney's peritubular cells, glomerular region or other regions of the kidney) increases the production of erythropoietin which in turn stimulates red blood cell production and alleviates anemia. In some configurations, the anemia treatment involves electrical stimulation of the renal nerve and/or the hypothalamus. In some configurations, the anemia therapy involves administering a drug to the patient. For example, the drug may comprise an erythropoietin stimulating agent or ESA, such darbepoetin alfa and/or epoetin alfa. The drug may be delivered to the patient by an electrically activated drug pump or drug patch.

The anemia therapy module 333 may develop a control signal based on information from the one or more blood parameter sensors to control the anemia therapy delivered to the patient. In one scenario, a blood viscosity sensor is used as a blood parameter sensor 312. Development of the therapy control signal may take into account thromboembolism risk as determined from the blood viscosity measurements.

Figure 3C:
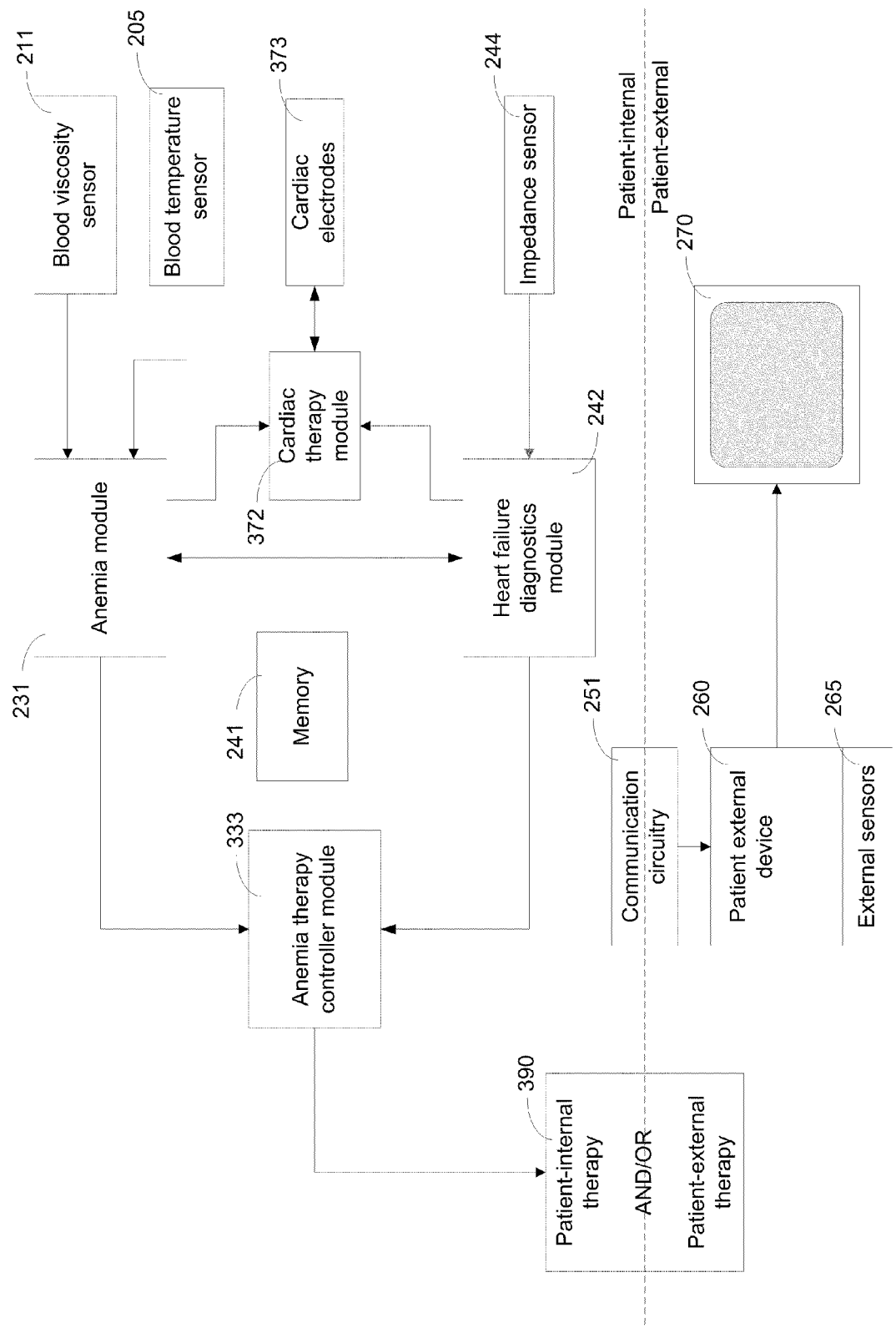
FIG. 3C is a block diagram illustrating a medical system that provides anemia monitoring and heart failure monitoring along with anemia therapy and cardiac therapy.

Some embodiments of the invention involve the delivery of anemia therapy along with the delivery of cardiac pacing therapy. FIG. 3C illustrates a medical system that includes anemia monitoring components such as components of FIG. 2B along with additional components for anemia and cardiac therapy. The medical system illustrated in FIG. 3C includes cardiac electrodes 373 electrically coupled to a heart which provide the capability of sensing cardiac signals and delivering electrical stimulation to cardiac tissue for pacing and/or other types of cardiac electrical stimulation therapy. A cardiac therapy module 372 includes circuitry that controls the delivery of the cardiac stimulation therapy via the cardiac electrodes 373 based on sensed cardiac signals and/or other information. For example, information provided by the heart failure diagnostics module 242 and/or the anemia module 231 may be taken into account in adjusting or initiating cardiac therapy.

Accordingly, in some configurations, the cardiac therapy module automatically processes the information regarding heart failure status and/or anemia status and adjusts the cardiac therapy in response to changes in the patient's anemia status and/or heart failure status. In some configurations, the anemia status and/or heart failure status is reported to the patient's health care provider via the patient external device 260. The health care provider may make adjustments to the patient's therapy by entering programming commands and uploading these to the cardiac therapy module. In some embodiments, the medical system may present the health care provider with certain options or recommended therapy parameters based on the anemia status information, the heart failure status information and/or other information about the patient which is manually entered into the system or automatically sensed by the system. In some implementations, cardiac resynchronization pacing therapy parameters may be recommended or cardiac resynchronization pacing therapy may be automatically initiated or adjusted by the cardiac therapy module 372 based on anemia status or detection of anemia.

In some embodiments, patient external sensors 265 are also provided via the patient external device. The patient external sensors 265 may include a weight sensor, blood pressure sensor, sensors for measuring red blood count, hemoglobin and/or hematocrit. For example, optical and/or laser scattering tests may be used to test the patient's hemoglobin and/or hematocrit level. Information provided by the patient external sensors 265 may be used by the anemia module 231 and/or the heart failure diagnostics module 342 for determining anemia and heart failure status, respectively. Information from the patient external sensors 265 may be used in combination with the information acquired from the patient internal sensors described herein to provide enhanced diagnostics.

The medical system illustrated in FIG. 3C includes an anemia therapy module 333. The anemia therapy module 333 is used to control delivery circuitry 390 for an external or internal anemia therapy. In some embodiments, the anemia therapy control may involve the release of anti-anemia drugs through a drug pump or electrically activatable patch. If the drug pump or patch includes patient-external therapy components 390, the anemia therapy module 333 may communicate wirelessly with these components 390 to control the drug therapy delivery. In alternative arrangements, the patient external device 260 may communicate with the drug pump or other therapy delivery component 390 to control the anemia therapy.

In some implementations, the anemia therapy module 333 may control an electrical stimulator 390 configured to provide patient-internal electrical stimulation therapy. For example, it is believed that electrical stimulation of kidney or brain structures aid in the production of red blood cells to alleviate anemia status. For example, the electrical stimulation therapy may be implemented to increase the production of erythropoietin which in turn stimulates the production of red blood cells thereby improving the patient's anemia status.

Figure 4:
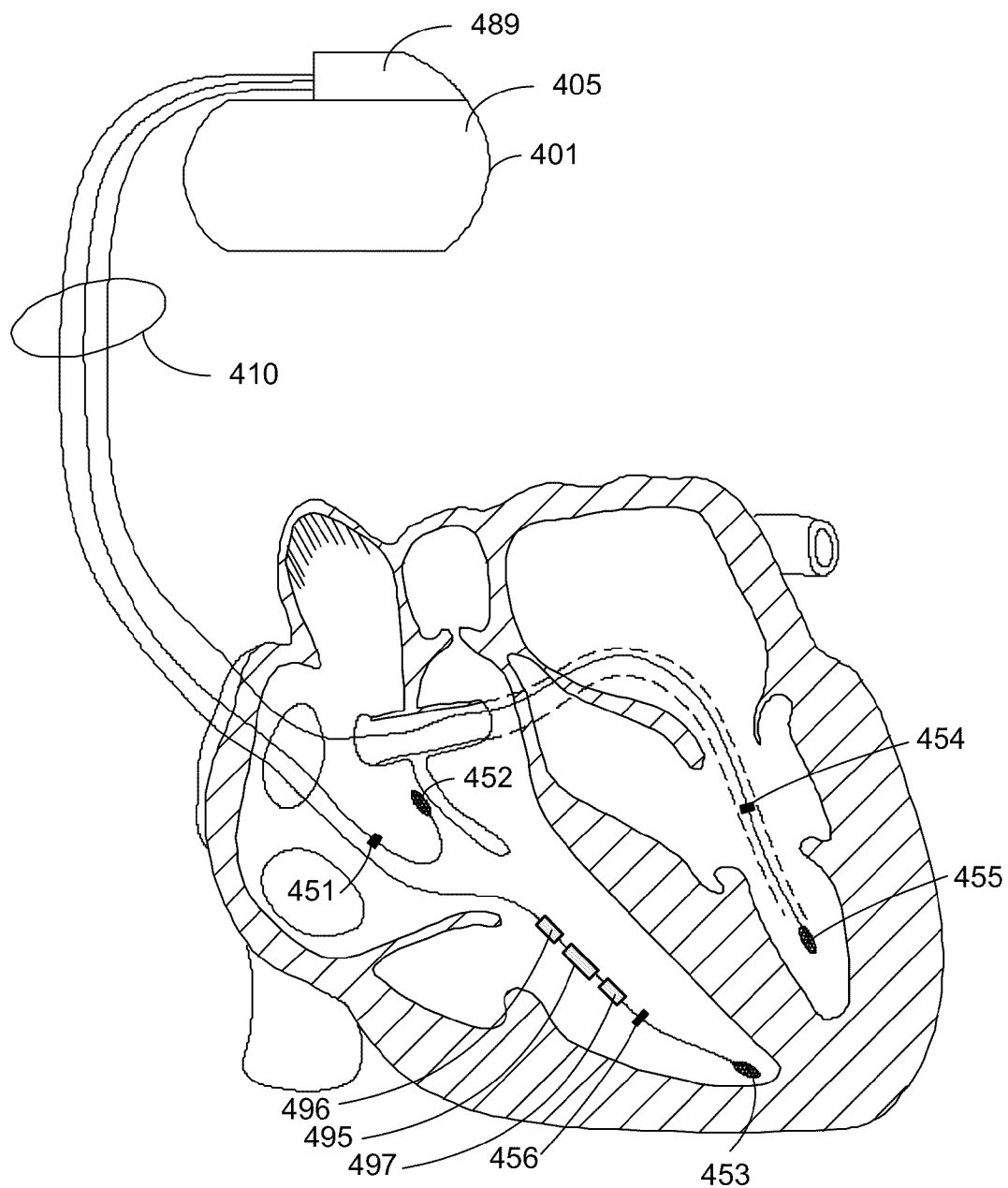
FIG. 4 shows a medical system that includes a blood viscosity sensor deployed on an intracardiac lead.

As previously discussed, blood viscosity may be used as a basis for anemia status determination and/or anemia detection. In some configurations, blood viscosity is measured using an acoustic sensor that is deployed in a blood vessel or cardiac chamber. FIG. 4 illustrates an intracardiac blood viscosity sensor 495 deployed on the lead system 410 of a cardiac rhythm management (CRM) device 405. Additional sensor circuitry involved in the generation of the blood viscosity signal, an anemia module, and/or an anemia therapy module may be incorporated within the housing 401 of the CRM device 405. The CRM device 405 may include circuitry for providing heart failure diagnostics, detecting cardiac arrhythmias and providing various cardiac electrical stimulation therapies, such as bradycardia pacing, rate adaptive pacing, anti-tachyarrhythmia pacing, defibrillation/cardioversion shocks, subthreshold cardiac stimulation, and/or cardiac resynchronization therapy.

As illustrated in FIG. 4, portions of the intracardiac lead system 410 are inserted into the patient's heart. The intracardiac lead system 410 includes a blood viscosity sensor 495 in addition to cardiac electrodes 451-456 configured to sense electrical cardiac activity of the heart and deliver electrical stimulation to the heart. Portions of the housing 401 of the cardiac device 405 may optionally serve as one or multiple can or indifferent electrodes. The cardiac electrodes 451-456 may also be used to sense the patient's thoracic impedance. Additional sensors may be deployed via the lead system 410. For example, the intracardiac lead system may include a pressure sensor 496 and/or a blood temperature sensor 497.

The cardiac electrodes 451-456 and sensors 495-497 shown in FIG. 4 illustrate one possible arrangement. Many other arrangements, including intracardiac and/or subcutaneous intrathoracic and non-intrathoracic electrodes, may be used and are considered to fall within the scope of the invention. The lead system 410 may include wired and/or wirelessly coupled sensors. In wireless configurations, sensed signals from the sensors are wirelessly communicated to the implantable cardiac device 405 and/or may be wirelessly communicated to a patient-external device.

Figure 5:
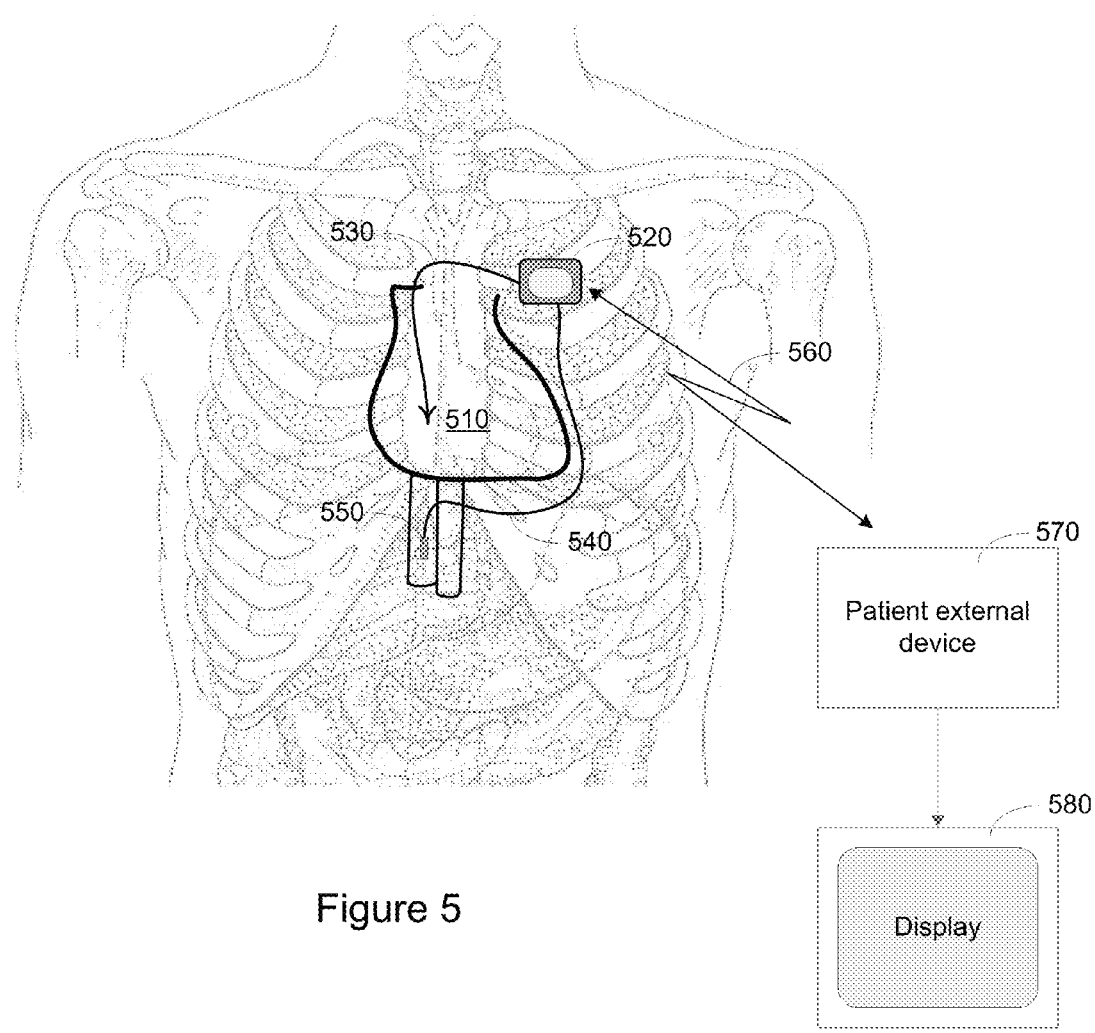
FIG. 5 illustrates a medical system that includes a blood viscosity sensor deployed within a blood vessel.

FIG. 5 illustrates an alternate embodiment of a medical system that includes a blood viscosity sensor 550 deployed within a blood vessel. In this embodiment, an implantable device (IMD) 520 is coupled to the blood viscosity sensor 550 and may also include an intracardiac lead system 530 disposed within one or more chambers of the heart 510. The IMD 520 may have sensing, monitoring and therapy capabilities for monitoring cardiac activity and/or delivering cardiac therapy by electrical stimulation delivered to the heart via the intracardiac lead system 530. As illustrated by FIG. 5, the blood viscosity sensor 550 may be disposed within a blood vessel, such as the inferior vena cava, the superior vena cava. The blood viscosity sensor 550 is coupled via a lead 540 to an anemia module which can be disposed within the housing of the IMD 520. The IMD 520 is communicatively coupled via a wireless link 560 to a patient external device 570 and optional display 580.

Figure 6:
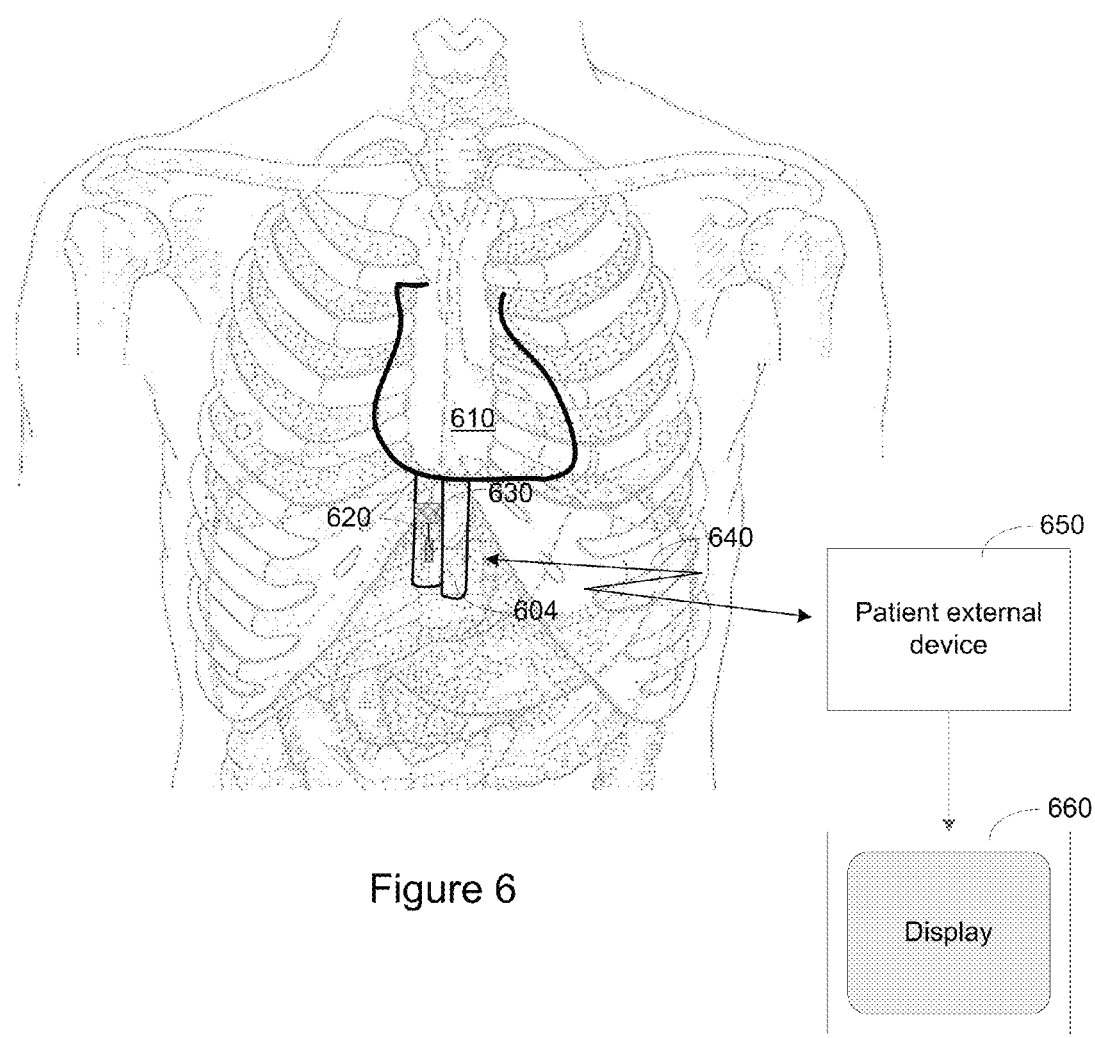
FIG. 6 illustrates a medical system that provides anemia status monitoring using a wireless sensor deployed in a blood vessel and communicatively coupled to a patient external device.

FIG. 6 illustrates an embodiment of a medical system that provides anemia status monitoring. The system includes a blood viscosity sensor 620 deployed within a blood vessel and secured by an anchor 630. The blood viscosity sensor 620 includes communications circuitry capable of establishing a wireless communications link 640 between the viscosity sensor 620 and a patient external device 650 and display 660. The blood viscosity sensor 620 may be powered, for example, by RF energy emitted by a sensor reader which is a component of the patient external device 650. The blood viscosity sensor 620 is capable of sensing blood viscosity and transmitting a signal indicative of blood viscosity to the external device 650.

In some implementations, the blood viscosity sensor 620 senses viscosity and transmits a signal that varies with blood viscosity to the patient external device 650 where the anemia module is deployed. For example, in come configurations, the frequency of the signal generated by the viscosity sensor 620 may vary with blood viscosity.

In some implementations, the viscosity sensor 620 is deployed in the blood vessel along with the anemia module circuitry. This additional circuitry may require additional energy storage capabilities for the patient internal components, such as a battery or rechargeable power source. In this implementation, the signal transmitted to the patient-external device 650 may include information derived from the sensed blood viscosity and possibly stored, such as measurements of hematocrit derived from the sensed signal, anemia status and/or anemia events which are determined from sensed blood viscosity, for example.

Figure 7A:
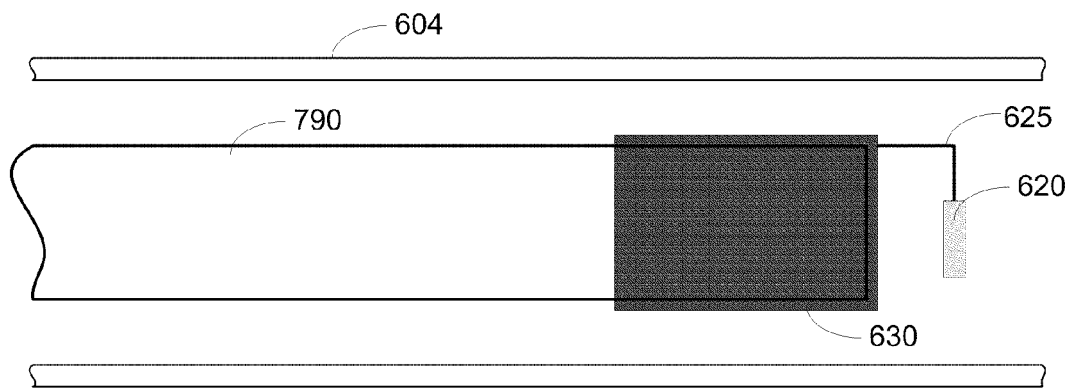
FIGS. 7A-7C illustrate various views of an expandable anchor configured to secure a viscosity sensor within a blood vessel.
Figure 7B:
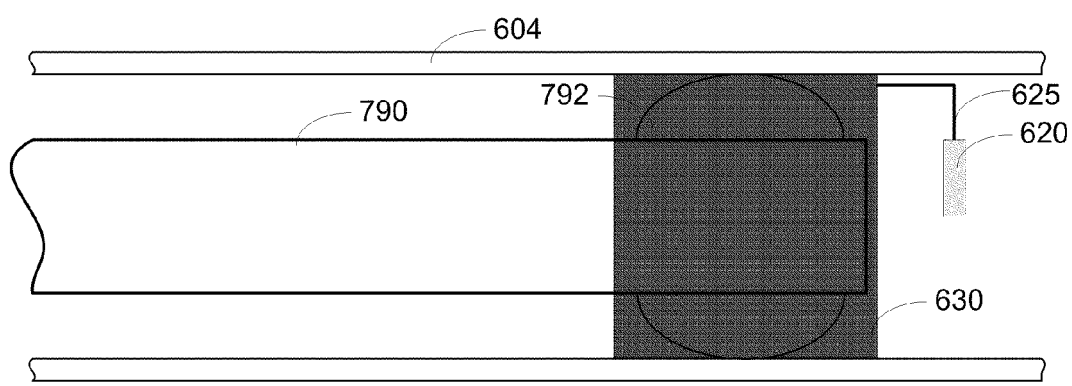
Figure 7C:
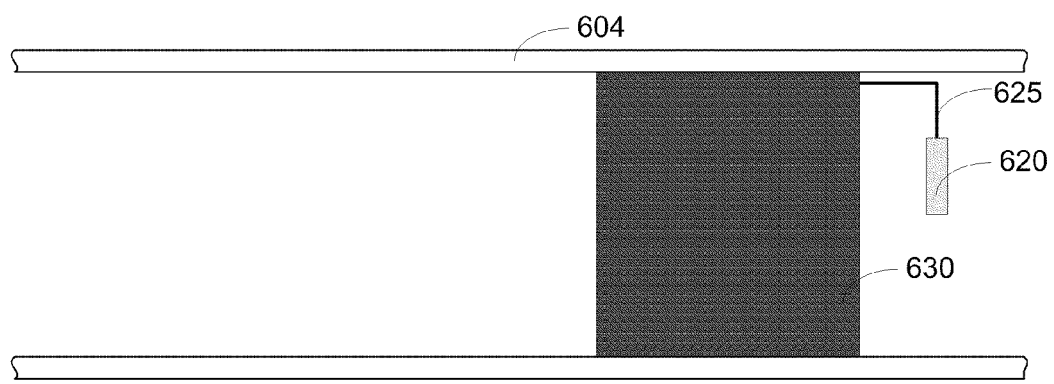

FIGS. 7A-7C illustrate in more detail an expandable anchor 630 configured to secure the viscosity sensor 620 in the blood vessel 604. The viscosity sensor 620 is secured to the expandable anchor 630 by a tether 625. The expandable anchor 630 may comprise a stent-like structure including a mesh surface that can be intravascularly delivered in a collapsed state (FIG. 7A) when inserted into the blood vessel 604. In this example, the expandable anchor 630 is coupled at or near the distal portion of a catheter 790. To expand the expandable anchor 630, the catheter 790 may include an inflatable balloon 792 which can be inflated after the viscosity sensor 620 is positioned appropriately in the blood vessel 604. Inflating the balloon 792 expands the expandable anchor 630 until the expandable anchor 630 abuts a wall of the blood vessel 604. The expandable anchor 630 abuts the wall of the blood vessel 604 with sufficient force to passively fixate the expandable anchor 630 and the blood viscosity sensor 620 in the blood vessel 604. Once the expandable anchor 630 is expanded and fixated in the blood vessel 604, the balloon 792 may be deflated to facilitate removal of the catheter 790 from the blood vessel 604. Additional anchoring techniques appropriate for blood viscosity sensors are described in commonly owned U.S. Patent Publication No. 20090025459 which is incorporated herein by reference.

Figure 8A:
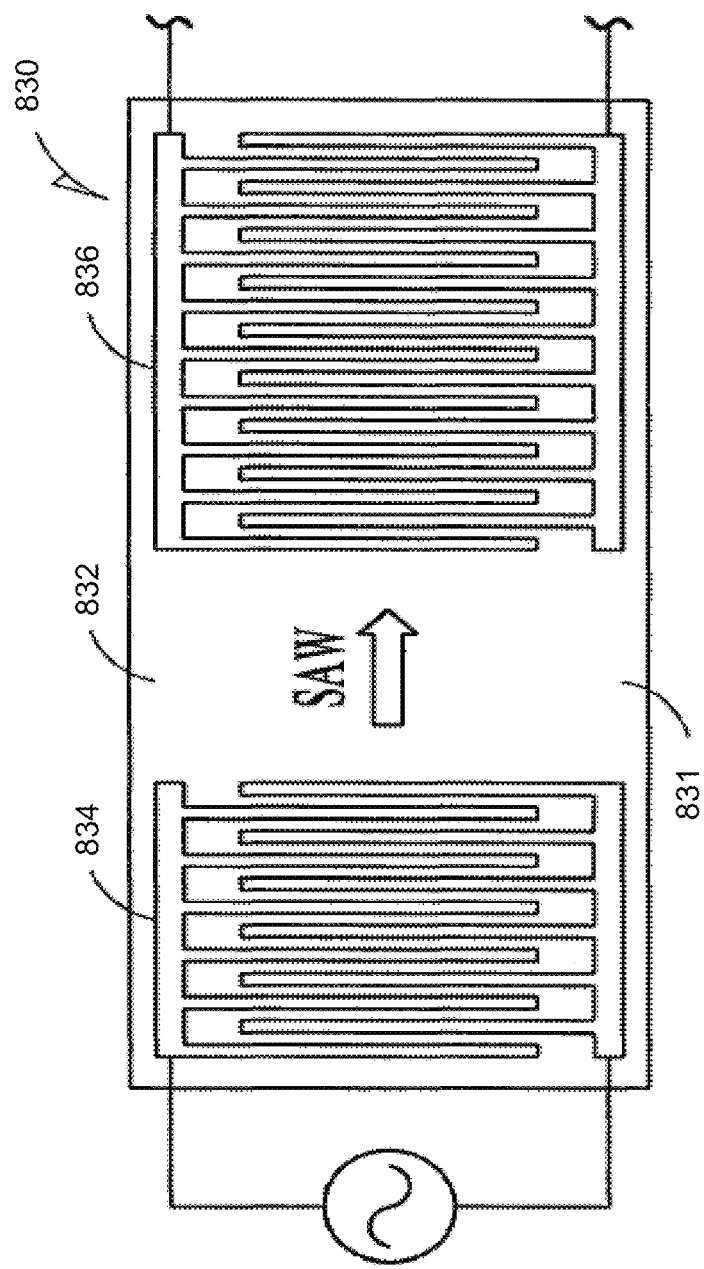
FIG. 8A depicts a piezoelectric surface acoustic wave (SAW) sensor configured to sense blood viscosity.

Referring to FIG. 8A, in one example, the blood viscosity sensor comprises piezoelectric surface acoustic wave (SAW) sensor 830. In this example, a sensor surface 832 includes a piezoelectric layer 831 having coupled thereto input interdigitated electrodes 834, output interdigitated electrodes 836, and an insulation layer. In one example, at least the input and output electrodes 834, 836 are coupled to a top of the piezoelectric layer 831. In this example, at least one of interdigitated electrodes 834 is driven with, for instance, an alternating voltage signal to activate the SAW transducer and generate surface acoustic wave along the surface 832 at a frequency. The vibrating surface 832 is in contact with a fluid, such as blood. In this example, the viscosity of the blood alters the oscillation frequency of the surface 832. For instance, an increased blood viscosity results in a lower oscillation frequency, and a decreased blood viscosity results in a higher oscillation frequency. The blood in contact with the surface 832 also causes resonance damping and an insertion loss due to the acoustic wave transferred to the blood, which can be related to the viscosity of the blood. This oscillation frequency shift or the power insertion loss can be used to create a viscosity signal, which can be converted into a viscosity measurement of the blood. In certain examples, SAW sensors 830 have different surface acoustic wave modes by choosing different piezoelectric material orientations. For instance, in one example, the sensor 830 operates in a shear vertical surface acoustic wave (SV-SAW) mode in which transverse displacement of the SAW is normal to the surface 832. In one example, the sensor 830 operates in a shear horizontal surface acoustic wave (SH-SAW) mode in which transverse displacement of the SAW is parallel to the surface 832.

Figure 8B:
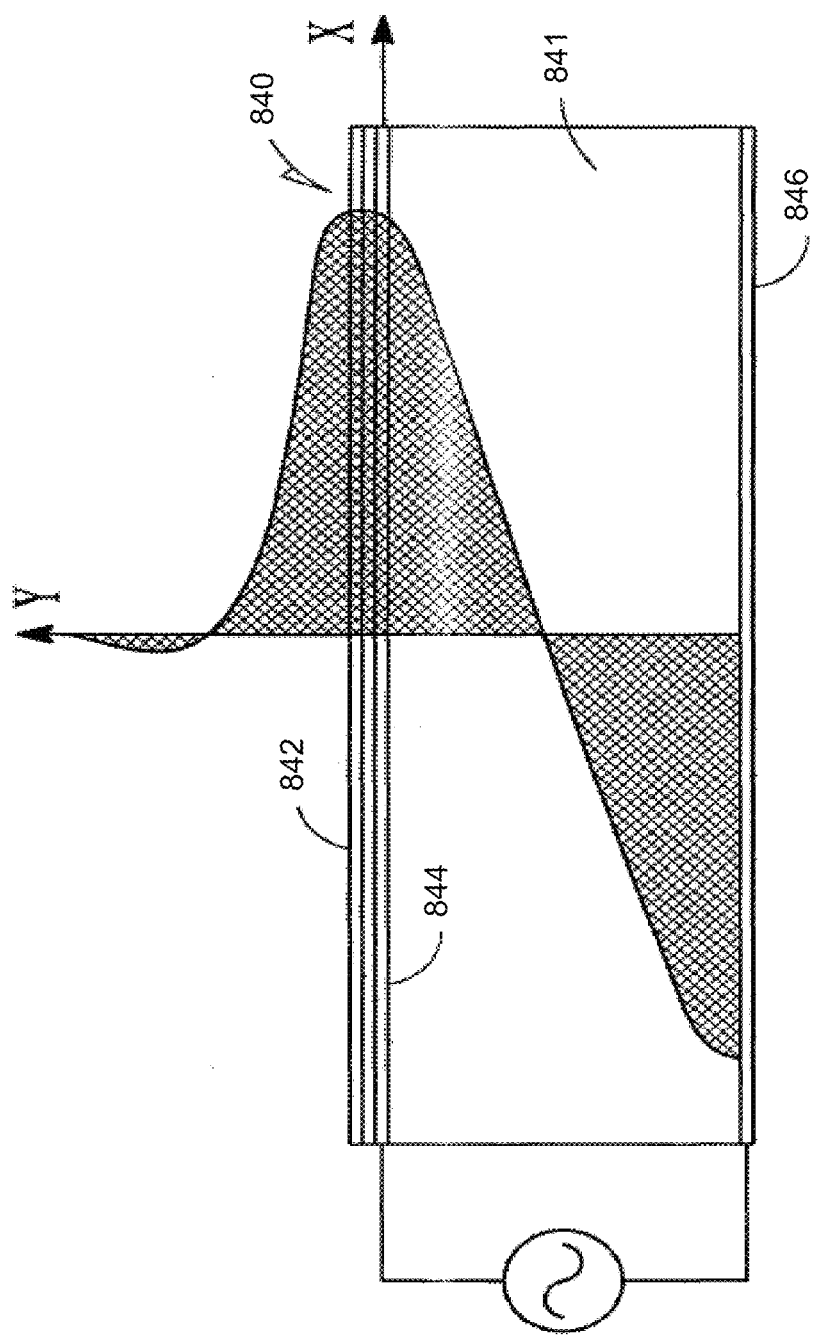
FIG. 8B depicts a bulk acoustic wave (BAW) sensor configured to sense blood viscosity.

Referring to FIG. 8B, in another example, the acoustic viscosity sensor comprises a bulk acoustic wave (BAW) sensor 840. Examples of BAW sensors include, for instance, a thickness shear mode (TSM) resonator and a shear-horizontal acoustic plate mode (SH-APM) sensor. In certain examples, the BAW sensor 840 includes a piezoelectric layer 841 sandwiched between top and bottom thin film electrodes 844, 846. In this example, an alternating voltage is applied to the electrodes 844, 846 to vibrate the piezoelectric layer 841 in a thickness shear mode at a frequency. Fluid, such as blood, in contact with the vibrating surface 842 mechanically interacts with the vibrating surface 842. A curve is depicted in FIG. 8B that represents displacements across a cross section of the BAW sensor 840, the fluid, and a solid-liquid interface therebetween. It is contemplated that the surface 842 is vibrated at the fundamental frequency, although it should be understood that other frequencies can be used or can result, such as harmonics. As in the example of the piezoelectric SAW sensor 830 above, the viscosity of the blood alters the oscillation frequency of acoustic wave, with, for instance, an increased fluid viscosity resulting in a lower oscillation frequency and a decreased fluid viscosity resulting in a higher oscillation frequency. The blood in contact with the surface 842 causes resonance damping and a frequency shift, which can be related to the viscosity of the blood. In an example, using the frequency change, the acoustic viscosity sensor 840 creates a signal that can be converted into a viscosity measurement of the blood.

In one example, an acoustic blood viscosity sensor comprises a microelectromechanical system (MEMS) based sensor. In one example, the MEMS based sensor comprises a solid-state acoustic wave transducer that is manufactured using a micro-machining process. In one example, the MEMS sensor comprises a solid-state surface acoustic wave (SAW) transducer. In another example, the MEMS sensor comprises a solid-state bulk acoustic wave (BAW) transducer. In these examples, a transducer of either of the acoustic sensors 830, 840 can be manufactured together with signal processing or conditioning electronics in one die. In another example, a transducer of either of the sensors 830, 840 can be packaged together with signal processing or conditioning electronics in one package. In another example, the acoustic viscosity sensor includes only the transducer of either of the acoustic sensors 830, 840, with the signal processing or conditioning electronics located in another device, either within or outside of the patient. In one example, the sensor and electronics are packaged in a titanium or other biocompatible material housing or box with the sensing surface exposed. In certain examples, the sensor packaging includes a coating of a drug eluting substance. In one example, the sensor packaging includes a coating of a drug eluting substance at least at the sensing surface.

Some configurations involve a medical device that has the capability to provide electrical stimulation therapy to one or more body structures to treat anemia. As discussed above, the kidneys are a primary site of production of the hormone erythropoietin which in turn is responsible for causing the bone marrow to produce red blood cells. Electrical stimulation therapy to affect renal function including erythropoietin production is discussed in commonly owned U.S. Publication 20080119907 which is incorporated herein by reference. U.S. Publication 20080119907 describes modulating renal function through electrical stimulation of one or more of a glomerulus, a Bowman's capsule, a macula densa, a tubule, a peritubular capillary network, a collecting duct, an afferent arteriole, an efferent arteriole, or a renal granular cell. For example, the peritubular cells may be a suitable site for erythropoietin stimulation. According to some studies, the peritubular cells of the kidneys are a site of erythropoietin synthesis. See, e.g., Lacombe, Catherine et al., *Peritubular cells are the site of erythropoietin synthesis in the murine hypoxic kidney*, J. Clin. Invest. Vol. 81, February 1988, 620-623. It has been shown that the renal sympathetic nerve is at least partially responsible for erythropoietin production. See, e.g., Tilmann Ditting, et al., *Renal sympathetic nerves modulate erythropoietin plasma levels after transient hemorrhage in rats*, Am J Physiol Renal Physiol 293: F1099-F1106, 2007.

A therapy for anemia involves electrical stimulation of kidney structures. The electrical stimulation is believed to increase erythropoietin production and thereby increase red blood cell concentration to alleviate the anemia. In some embodiments, the electrical energy stimulation is applied to one or more renal structures, e.g., a glomerulus, a peritubular capillary network, or a renal nerve thereby modulating the production of erythropoietin.

Figure 9:
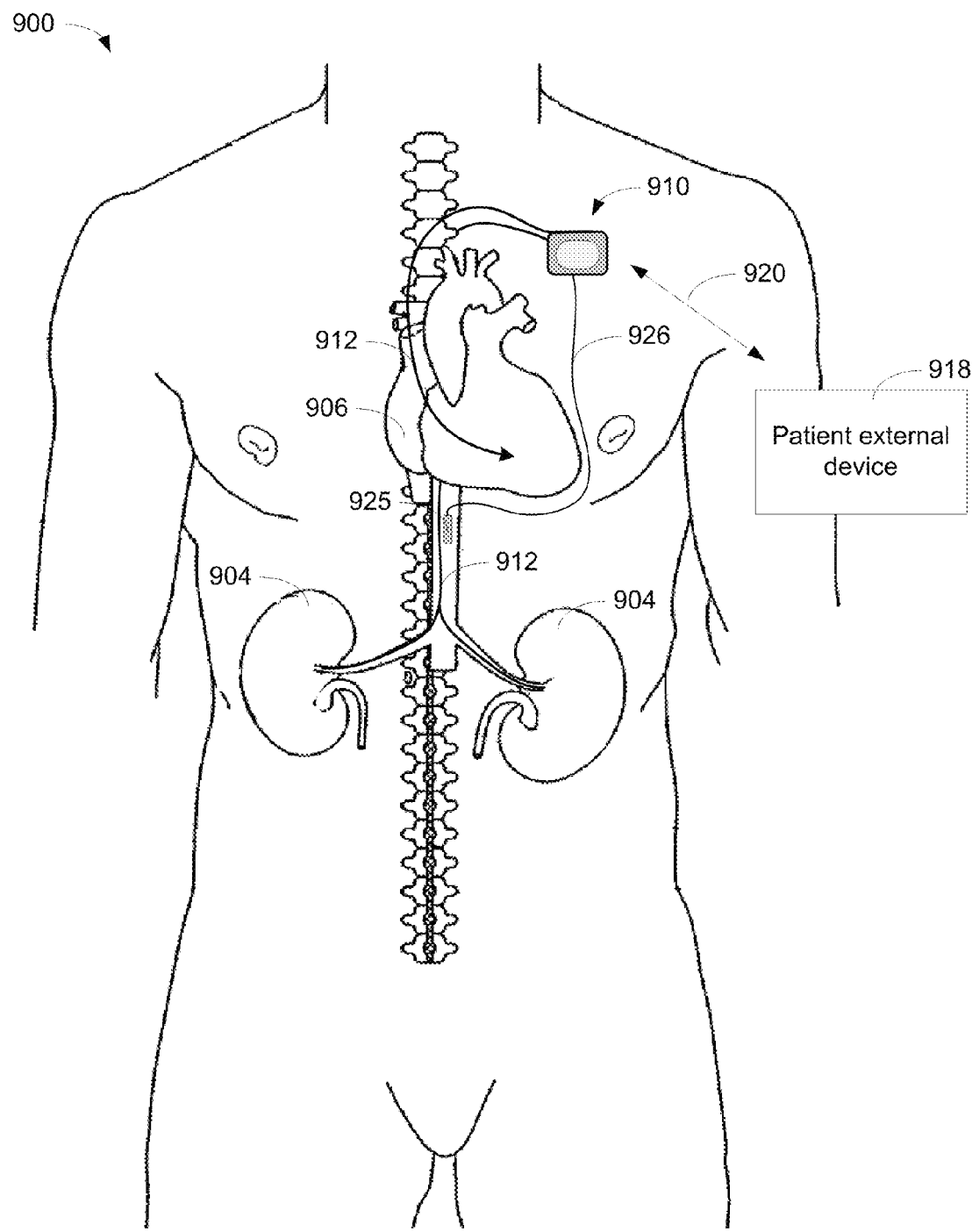
FIG. 9 illustrates a medical system capable of delivering electrical energy stimulation to one or both kidneys and/or the heart.

FIG. 9 illustrates one embodiment of a medical system 900 having the capability to deliver electrical energy stimulation to one or more portions of a subject's body, such as one or both kidneys 904. Optionally, the medical system may also have the capability of delivering electrical stimulation to the heart 906. In this embodiment, the system 900 includes an implantable medical device (IMD) 910, such as a pulse generator including cardiac therapy capabilities (e.g., capable of providing one or more of bradycardia therapy, tachycardia therapy, or cardiac resynchronization therapy), which is coupled by one or more leads 912 to the kidneys 904, the heart 906, and/or other body structures. The IMD 910 may be implanted subcutaneously in the subject's chest, abdomen, or elsewhere. Leads 912 for applying stimulation to the kidneys extend from a lead proximal end portion to a lead distal end portion, the latter of which includes one or more electrodes for delivering the electrical energy stimulation generated by the IMD 910 to the kidney(s) 904.

The medical system 900 also includes a one or more sensors 925, such as a blood viscosity sensor or blood impedance sensor that is used to develop a feedback signal to control the electrical stimulation delivered to the kidney 904. In the configuration illustrated in FIG. 9, the sensor 925 is electrically coupled to the IMD 910 through a lead 926, although a wireless connection is also possible. As previously discussed, an anemia module within the IMD 910 receives the sensor signal generated by the sensor 925. The anemia module may use the sensor signal to detect anemia, to determine anemia status, and/or to develop a feedback signal to control the electrical stimulation therapy delivered to the kidney 904.

The medical system 900 shown also includes a patient external device that serves as an external user interface 918. The external user interface 918 may receive information from, or send information to, the IMD 910. For instance, new values for one or more electrical energy parameters (e.g., an energy injection location, an energy injection duration, an energy injection intensity, an energy injection frequency, an energy injection polarity, an energy injection electrode configuration, or an energy injection waveform) applied to one or more kidney structures (e.g., a glomerulus, a Bowman's capsule, a macula densa, a tubule, a peritubular capillary network, a collecting duct, an afferent arteriole, an efferent arteriole, a renal granular cell, or a renal nerve) may be manually input into the external user interface 918 and sent to the IMD 910 to change a parameter of the electrical energy stimulation resulting in a desired change of the erythropoietin production of the kidneys. Additionally, the external user-interface 918 may be used to receive one or more inputs of the patient's health-related information. In certain embodiments, the external user interface 918 is used to externally process information for the system 900. Using telemetry, the external user-interface 918 may wirelessly communicate 920 with the IMD 910. The external user-interface 918 may include a visual or other display unit such as an LCD or LED display, for textually or graphically displaying information to the patient or a health care provider regarding operation or findings of the system 900.

Figure 10:
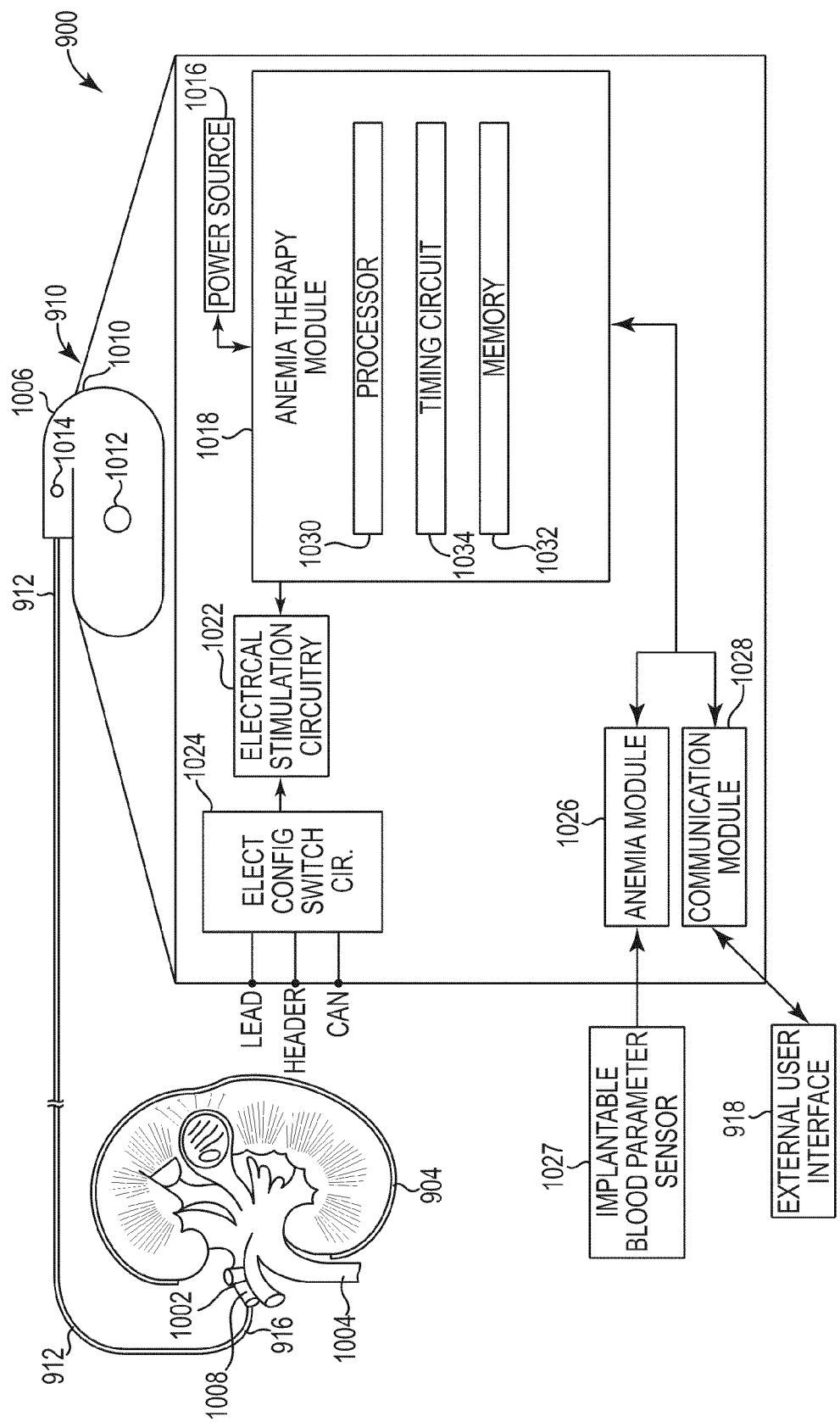
FIG. 10 illustrates a medical system configured to deliver electrical energy stimulation to a patient's kidney(s)

The simplified block diagram of FIG. 10 illustrates one conceptual embodiment of the system 900, which may deliver the electrical energy stimulation to the patient's kidney(s) 904. As shown, the system 900 includes an IMD 910, such as a pulse generator, coupled via one or more leads 912 to one or both kidneys 904. In this embodiment, the one or more leads 912 provide vascular access to the kidney 904 via a renal vein 1002.

Each lead 912 extends from a lead proximal end portion, which is coupled to an insulating header 1006 of the IMD 910, to a lead distal end portion 916, positioned within the renal region. Each lead distal end portion 916 includes one or more electrodes 1008 for delivering the electrical energy stimulation generated by the IMD 910 to the kidneys. The one or more electrodes 1008 may also be used for sensing information about one or more renal function-associated parameters. In addition to the lead electrodes 1008, other electrodes usable in the delivery of the electrical energy stimulation may be located on a hermetically-sealed enclosure 1010 of the IMD 910 (typically referred to as a can electrode 1012) or on the insulating header 1006 (typically referred to as a header electrode 1014).

As shown, the IMD 910 includes electronic circuitry components that are enclosed within the hermetically-sealed enclosure 1010, such as an anemia therapy module 1018, a power source 1016, electrical stimulation circuitry 1022, an electronic configuration switch circuit 1024, an anemia module 1026, and a communication module 1028. The power source 1016 provides operating power to all of the aforementioned IMD internal modules and circuits.

The anemia therapy module 1018 includes, among other things, a processor 1030, a memory 1032, and a timing circuit 1034. The processor 1030 is configured to determine therapy control signal using information about the patient's anemia status. The therapy control signal is subsequently communicated to the electrical stimulation circuitry 1022, which is configured to generate an electrical energy signal deliverable by one or more chosen electrodes 1008, 1012, or 1014 to the kidney 904. In various examples, the one or more delivery electrodes are chosen such that a substantially large portion of the electrical energy signal passes through one or more kidney structures (e.g., a glomerulus, a Bowman's capsule, a macula densa, a tubule, a peritubular capillary network, a collecting duct, an afferent arteriole, an efferent arteriole, or a renal granular cell). The electrical stimulation circuitry 1022 is selectively coupled to the one or more electrodes 1008, 1012, or 1014 by the electronic configuration switch circuit 1024.

The electrical energy stimulation may be delivered to the kidney 904 in various ways. For instance, the electrical energy stimulation delivered to the kidney 904 by the electrodes 1008, 1012, or 1014 includes a frequency between about 0.1 Hz and about 10 KHz. In one such embodiment, the signal frequency is delivered in one or more bursts having a burst frequency substantially less than 1 KHz, such as around 1 Hz. In another embodiment, the electrical energy stimulation delivered to the kidney 904 by the electrodes 1008, 1012, or 1014 includes a frequency of greater than about 50 KHz. In yet another embodiment, the electrical energy stimulation delivered to the kidney 904 by the electrodes 1008, 1012, or 1014 includes a continuous periodic or pulsed periodic electric current or voltage.

The medical system 900 illustrated in FIG. 10 provides for ongoing adjustment of the electrical stimulation therapy delivered by the electrical stimulation circuitry 1022 via a feedback signal provided using the blood parameter sensor. The implantable blood parameter sensor 1027 continuously or periodically measures a blood parameter related to anemia, such as blood viscosity or blood impedance, providing a sensor signal to the anemia module 1026. For example, if blood viscosity is the parameter sensed, the anemia module 1026 may compare a current level of the blood viscosity to a previous level to determine if the patient's blood viscosity is increasing or decreasing. As the blood viscosity changes, the anemia module communicates the patient's blood viscosity (or hematocrit value if it is calculated) and/or anemia status to the anemia therapy module 1018. If the patient's anemia status is deteriorating, the deterioration may trigger the anemia therapy module 1018 to modify the electrical stimulation therapy delivered to the kidneys 904 to provide a more aggressive therapy. On the other hand, if the patient's anemia status is improving, this may trigger the anemia therapy module 1018 to keep constant the electrical stimulation therapy delivered to the kidneys 904 or to provide a less aggressive therapy. Accordingly, the configuration of FIG. 10 provides for ongoing feedback and adjustment of the electrical stimulation therapy as the patient's anemia status changes.

The medical system 900 of this embodiment further includes a patient-external user-interface 918. The patient external user-interface 918 receives, for example, manually entered desired values related to anemia therapy and communicates the same to the IMD 910 via the communication module 1028. The manually entered values may be used in lieu of preprogrammed parameter values stored in the memory 1032. In some embodiments, the external user interface 918 may include or be linked to external sensors used to measure blood parameters. Information from the external sensors may be used to provide the feedback signal to control the electrical stimulation therapy.

The IMD 910 may include multiple individually programmable electrical stimulation channels wherein each stimulation channel is capable of being connected to multiple electrodes. The electrode configuration and stimulation characteristics for each channel may be automatically or manually selected. For example, each channel may be coupled to any number of electrodes. In addition, each channel may be separately programmable with regard to amplitude, pulse width, pulse amplitude, frequency, duty cycle, and phase shift with respect to other stimulation channel signals. This flexibility in stimulation characteristics allows closed loop feedback adjustment of the stimulation output of the medical system until a desired change in the anemia status of the patient is attained as indicated by the sensed blood parameters.

It is to be noted that FIG. 10 and other Figures depicted herein illustrate certain conceptualizations of various modules, circuits, and interfaces of various systems, which may implemented either in hardware or as one or more sequences of steps carried out on a microprocessor or other controller. Such modules, circuits, and interfaces are illustrated separately for conceptual clarity; however, it is to be understood that the various modules, circuits, and interfaces depicted need not be separately embodied, but may be combined or otherwise implemented.

Figure 11:
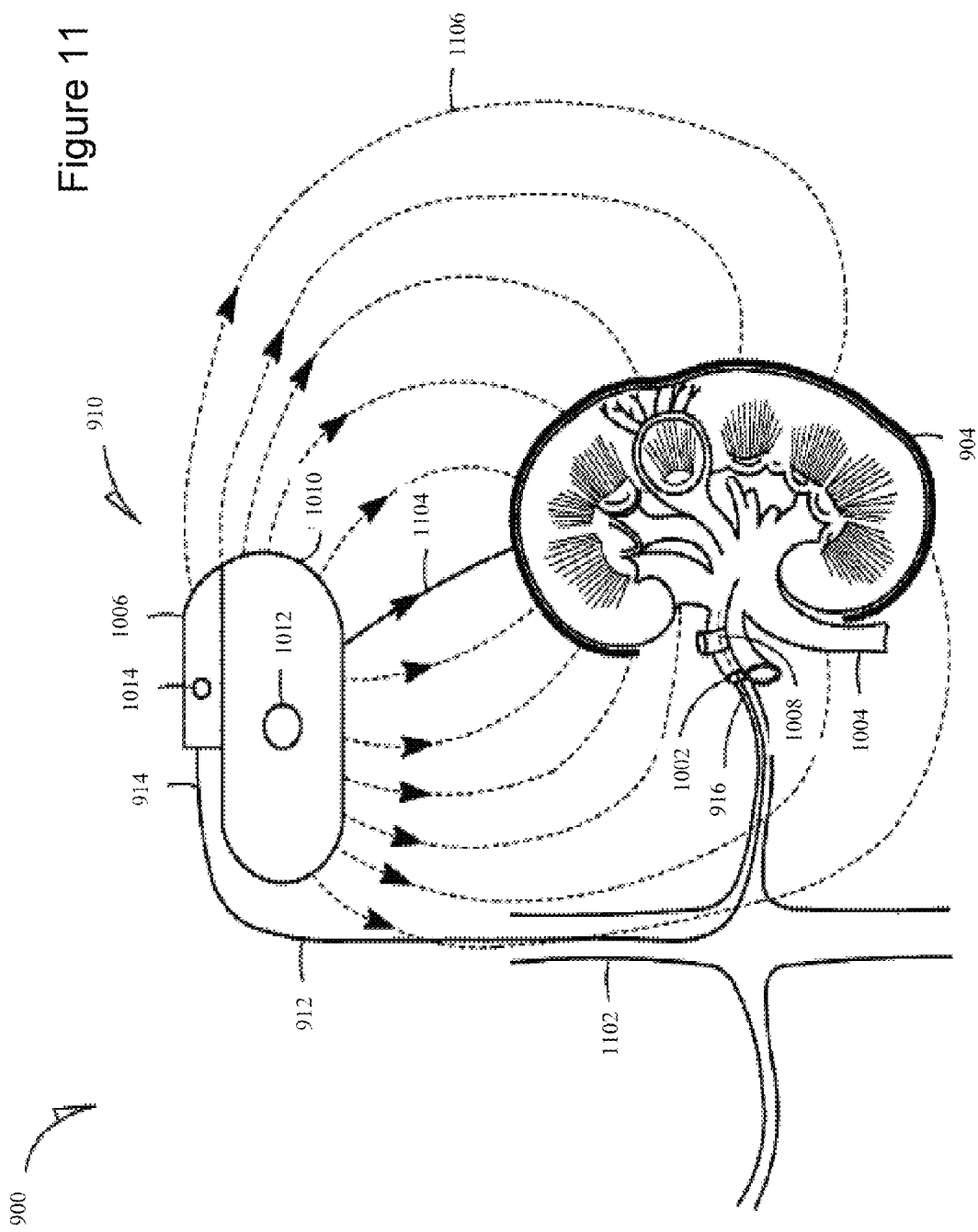
FIG. 11 shows energy stimulation delivery to the subject's kidney in the form of an electric current and an associated electric field.

FIG. 11 illustrates the system 900 in the process of delivering electrical energy stimulation in the form of an electric current 1104 and an associated electric field 1106 to the subject's kidney 904. In certain embodiments, the electrical energy stimulation includes a pulsed voltage signal with approximately a zero average amplitude, a frequency between about 0.1 Hz and about 1 MHz, and a peak-to-peak amplitude sufficient to produce an electric field strength of about 0.1 volts per centimeter to about 10 volts per centimeter.

The kidney 904 is a bean-shaped structure, the rounded outer convex of which faces the side of the subject's body. The inner, indented surface of the kidney 904, called the hilum, is penetrated by a renal artery, a renal vein 1002, nerves, and a ureter 1004, which carries urine out of the kidney 904 to the bladder. As shown, the system 900 includes an IMD 910 electrically coupled to the kidney 904 via at least one lead 912. The lead extends from a lead proximal end portion 914, where it is coupled to an insulated header 1006 of the IMD 910, to a lead distal end portion 916 disposed within the renal vein 1002. The lead distal end portion may include one or more electrodes for use in bipolar stimulation (not shown) or unipolar stimulation of the kidney structures. FIG. 11 illustrates unipolar stimulation wherein an electric field 1106 is developed between the can electrode 1012 and/or header electrode 1014 and a lead electrode 1008 disposed within or near the kidney. In this embodiment, the lead 912 is provided vascular access to the renal vein 1002 via the inferior vena cave 1102. In another embodiment, the lead distal end portion 916 is positioned deep within the kidney 904, such as in an arcuate vein, an interlobar vein, or a segmental vein. In yet another embodiment, the lead 912 may be delivered via a urethra-bladder-ureter 1004 access.

As shown, but as may vary, the lead distal end portion 916 includes at least one implanted electrode 1008 disposed proximal to the kidney 904 (i.e., within, on, or about the kidney 904), while the hermetically-sealed enclosure 1010 (via can electrode 1012) or the insulating header 1006 (via header electrode 1014) acts as another implanted electrode by being at least partially conductive. In this way, an electrical energy signal provided by the IMD 910 and delivered by the lead electrode 1008 disposed within, on, or about the kidney 904 may return through a portion of the kidney to the can 1012 or header 1014 electrode. In certain embodiments, the electrical energy stimulation is delivered in the form of an electric current 1104 having an associated electric field 1106.

The electric current 1104 and the associated electric field 1106 may be positioned such that one or more structures of the kidney 904 are immersed within the current 1104 or field 1106 sufficient to affect one or more renal functions, and more specifically, affect the generation of erythropoietin by the kidney. The present system 900 is adapted to work in a variety of electrode configurations and with a variety of electrical contacts (e.g., patches) or electrodes in addition to the electrode configuration shown in FIG. 11. For instance, multiple leads 912 may be placed in different kidney locations to improve the electric current 1104 or electric field 1106 distributions. Alternatively or additionally, lead 912 may have one or more additional electrodes wherein the one or more electrodes perform as the cathode for the electric current 1104 and associated electric field 1106, for example.

Figure 12:
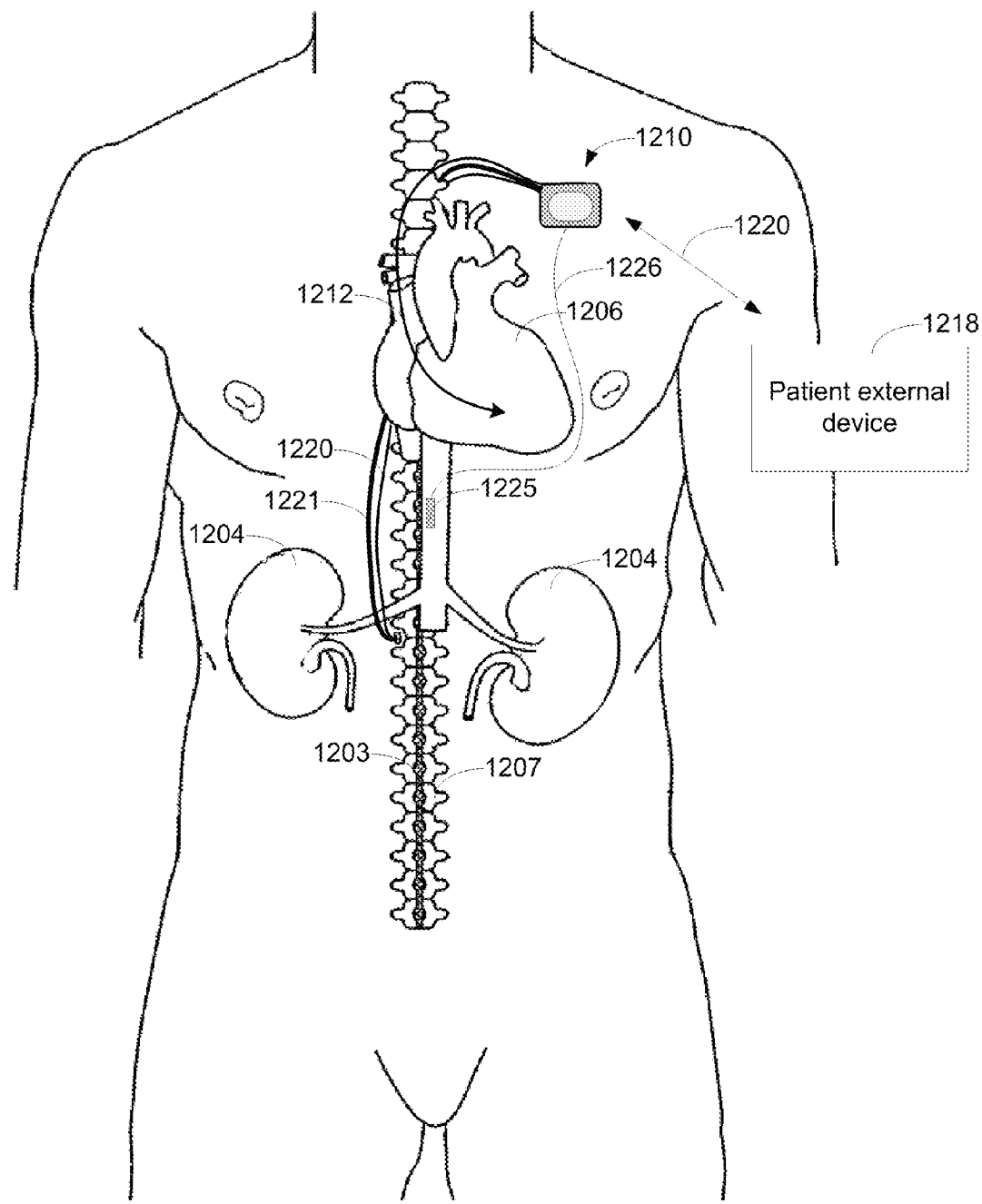
FIG. 12 illustrates a medical system configured to stimulate the renal nerve to treat anemia.

As discussed above, studies have shown that the renal nerve is important in the production of erythropoietin and is involved in maintaining blood hematocrit. Thus, treatment of anemia in accordance with some embodiments involves electrical stimulation of the renal nerve to influence erythropoietin production. FIG. 12 illustrates a medical system configured to stimulate the renal nerve via electrical stimulation pulses or by drug infusion. An IMD 1210 configured to stimulate the renal nerve may be an electrical device similar to a cardiac pacemaker or nerve stimulator and/or may be a chemical substance infusion device. As illustrated in FIG. 12, the IMD 1210 may be configured to serve a dual purpose by delivering cardiac stimulation therapy as well as electrical and/or drug infusion stimulation of the renal nerve. In some embodiments, the IMD 1210 only provides electrical stimulation of the renal nerve and does not have the capability of providing drug infusion to the renal nerve. In some embodiments, the IMD only provides drug infusion and does not have the capability to provide electrical stimulation to the renal nerve. Suitable drugs for promoting erythropoietin production include erythropoiesis-stimulating agents (ESAs).

As previously indicated in connection with FIG. 10, the IMD 1210 may include multiple individually programmable electrical stimulation channels wherein each stimulation channel is capable of being connected to multiple electrodes. The electrode configuration and stimulation characteristics for each channel may be automatically or manually selected. For example, each channel may be coupled to any number of electrodes. In addition, each channel may be separately programmable with regard to amplitude, pulse width, pulse amplitude, frequency, duty cycle, and phase shift with respect to other stimulation channel signals. This flexibility in stimulation characteristics allows closed loop feedback adjustment of the stimulation output of the medical system until a desired change in the anemia status of the patient is attained as indicated by the sensed blood parameters.

The IMD 1210 includes a power supply and control circuitry used to regulate the electrical signal(s) delivered to the renal nerve and/or to control the drug infusion operation. If drug infusion is employed, the IMD 1210 includes a reservoir with medication. A lead 1220 attached to the IMD electrical stimulation circuitry carries the electrical signal to one or more electrodes at the distal end of lead 1220 implanted near or attached to the renal nerve. If drug infusion is provided, a catheter 1221 carries medication to an appropriate location of the renal nerve.

The renal nerve conducts efferent sympathetic stimulation from the sympathetic trunk 1203 to the kidney 1204. Sympathetic trunk 1203 is connected to the patient's spinal cord inside the spine 1207. The stimulation electrode and/or drug infusion location can be located between the kidney 1204 and the posterior renal or other renal ganglia (not shown) in the region of the $10^{th}$, $11^{th}$, and $12^{th}$ thoracic and $1^{st}$ lumbar segments of the spine 1207.

Electrical stimulation may be delivered to the renal nerve through one or more cuff electrodes or other type of electrode disposed near, on, or around the renal nerve. For example, one or more cuff electrodes may be disposed at the distal portion of lead 1220. These cuff electrodes wrap around the renal nerve to provide electrical contact between the electrode and the nerve so that electrical signals provided by the IMD 1210 are applied to the renal nerve. Other types of electrodes may alternatively be employed, such as helical electrodes.

The IMD 1210 is coupled to a sensor lead 1226 terminated with blood parameter sensor 1225. For example, the blood parameter sensor can be a blood viscosity or blood impedance sensor. The sensor 1225 can be located in a blood vessel or heart chamber. A blood parameter signal generated by the sensor 1225 is used to provide the IMD 1210 with information necessary to regulate the electrical stimulation signals to kidney 1204 and/or the drug infusion to influence erythropoietin production. More than one sensor can be used in combination to supply information to the IMD 1210. These sensors can be implanted inside the body or located outside the body. For example, in some embodiments, an external blood parameter sensor may be coupled via the patient external device 1218 to the IMD 1210. Information obtained form the external blood parameter sensor may be used to develop the feedback signal to control the electrical stimulation or drug infusion.

Figure 13:
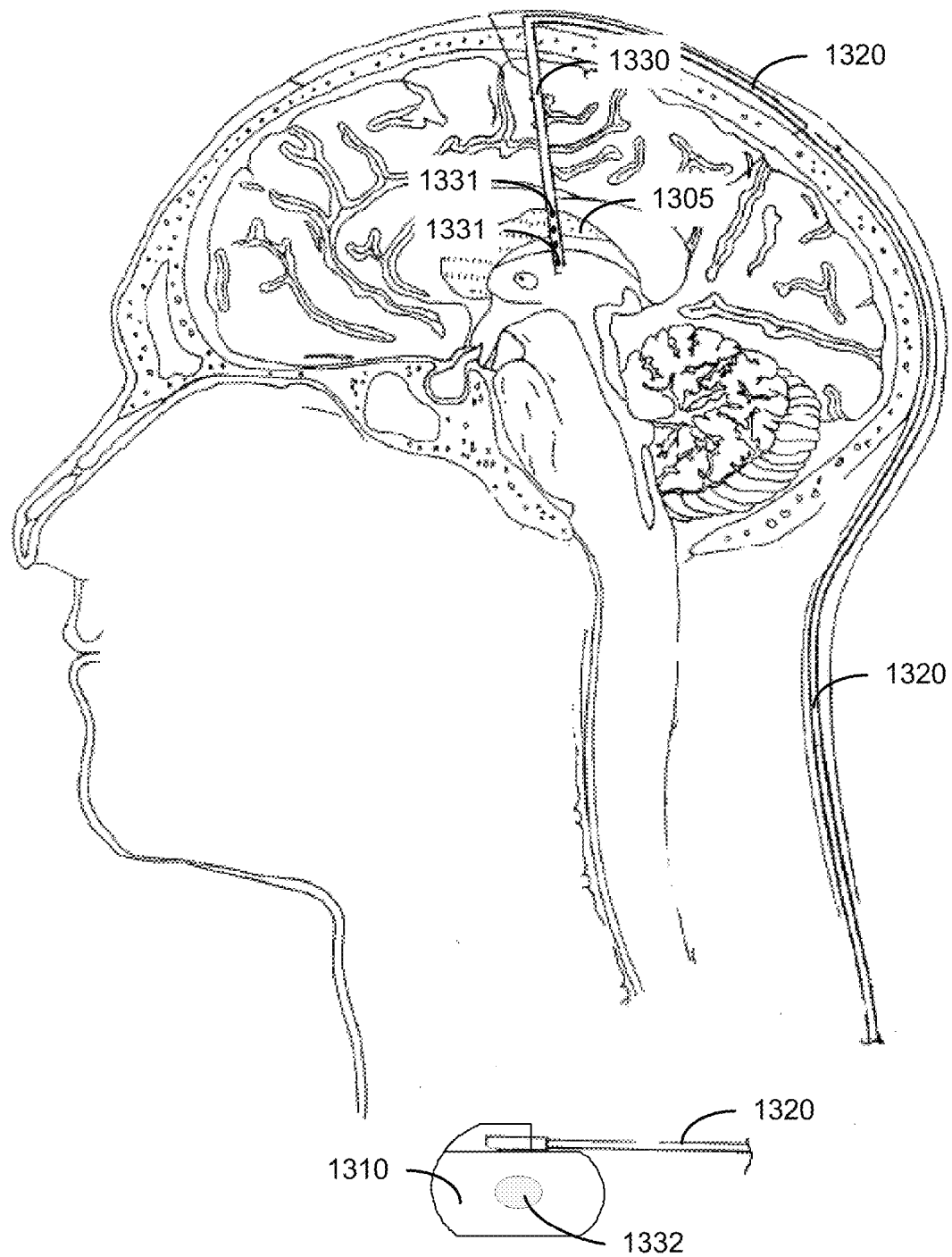
FIG. 13 is a diagram of a medical system configured to electrically stimulate the hypothalamus region of the brain to improve or stabilize anemia status.

Studies have indicated that stimulation of the hypothalamus and/or other deep brain locations are related to production of red blood cells. See, e.g., Segal, R. et al., *The effect of electrical stimulation of the hypothalamus on red cell production and destruction in the rat*, Isr J Med Sci, 1971 July-August; 7(7):1017-24; Medado P, Izak G, Feldman S., *The effect of electrical stimulation of the central nervous system on erythropoiesis in the rat. II. Localization of a specific brain structure capable of enhancing red cell production*, J Lab Clin Med 1967 May; 69(5):776-86; Segal, R., Izak G., Feldman S., *Augmented red cell sequestration after prolonged electrical stimulation of the posterior hypothalamus in rats.*, J Reticuloendothel Soc 1971 March; 9(3):225-36; Halvorsen, S., *Effects of hypothalamic stimulation on erythropoiesis and on the production of erythropoiesis-stimulating factors in intact and nephrectomized rabbits*, Ann N Y Acad Sci, 1968 Mar. 29; 149(1):88-93. These brain regions may be electrically stimulated to increase red blood count. FIG. 13 provides one such example related to electrical stimulation of the hypothalamus.

FIG. 13 illustrates a medical system 1300 configured to electrically stimulate the brain in the hypothalamus region 1305 to improve or stabilize anemia status. The system 1300 comprises an IMD 1310 that includes an electrical stimulator such as the electrical stimulator previously discussed with regard to FIG. 12. The IMD 1310 may be implanted in a pectoral region with a lead 1320 that runs to an appropriate location for accessing the hypothalamus 1305. Regions other than the pectoral region, such as the abdomen may alternately be used as the implant site for the IMD 1310.

The lead 1320 is coupled to the IMD 1310 and to an electrode array 1330 which is inserted through the brain to reach the hypothalamus region 1305. The electrode array 1330 may include multiple electrodes 1331 to provide for selection of the electrode configuration that provides the desired response in anemia status. One or more additional electrodes 1332 may be provided on the housing of the IMD 1310. Switching circuitry within the IMD 1310 allow any combination of electrodes to be selectively coupled to any stimulation channel. The stimulation characteristics are also independently adjustable for each channel. The IMD 1310 may incorporate a multichannel electrical stimulator that can automatically adjust electrode configuration and/or the stimulation characteristics of each channel based on closed loop feedback from the blood parameter sensor (not shown in FIG. 13) until a desired change in anemia status is detected. Stimulation characteristics include stimulation amplitude, polarity, pulse width, duty cycle, frequency, phase and/or other stimulation characteristics.

In some embodiments, the IMD 1310 automatically adjusts the anemia therapy. In some embodiments, the IMD 1310 may not utilize automatic feedback control, but may be controlled manually through a patient external programmer by the patient or the patient's health care provider. In another configuration, the IMD 1310 may utilize both manual and automatic adjustments of the electrode configurations and stimulation characteristics.

Figure 14:
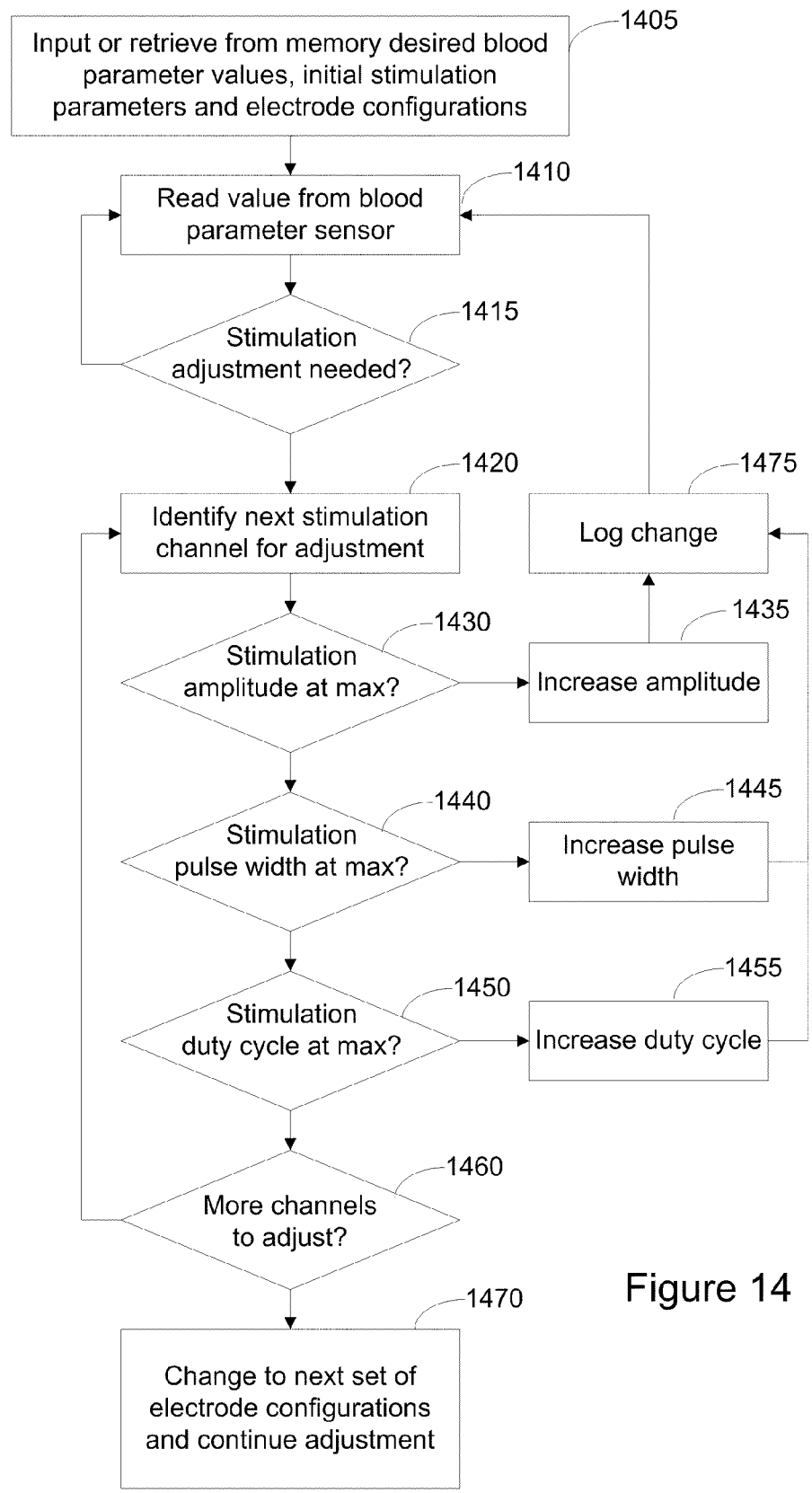
FIG. 14 is a flow diagram illustrating a feedback process for stimulation of the kidney, renal nerve, hypothalamus, and/or other body structures for the treatment of anemia.

FIG. 14 is a flow diagram illustrating a feedback process for stimulation of the kidney, renal nerve, hypothalamus, and/or other body structures for the treatment of anemia. Initially, blood parameter threshold values indicative of a desired anemia status are input or read 1405 from memory. The initial stimulation parameters are also retrieved along with an initial set of electrode configurations for each channel and the order in which the stimulation channels will be adjusted. The signal generated by the blood parameter sensor is obtained 1410 and the blood parameter is compared to the threshold values. Deviations above or below the threshold indicate the need for adjustment. If adjustment is required 1415, the amplitude of the first stimulation channel is adjusted 1435, unless 1430 the channel is at a maximum amplitude. If the stimulation channel is at maximum amplitude, then the pulse width is adjusted 1445. If the pulse width is 1440 at a maximum value, the duty cycle is adjusted 1455. If all stimulation parameters are 1450 at maximum for the channel, and there are more channels to adjust 1460, then the next channel is adjusted. If all stimulation channels are at their maximum values, then a different set of electrode configurations is identified 1470 and adjustment proceeds according to steps 1420-1460 until the desired blood parameter value is achieved. Changes to the stimulation parameters are logged 1475. The stimulation configuration identified by the feedback process may be used as a starting point for a subsequently delivered therapy.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical system, comprising:
an implantable sensor including circuitry configured to sense blood viscosity and to generate a signal modulated by the blood viscosity;
implantable circuitry configured to receive the blood viscosity signal and to store the blood viscosity; and
an anemia module coupled to the implantable circuitry, the anemia module configured to compare the blood viscosity to one or more thresholds associated with hematocrit, to determine an anemia status of a patient based on the comparison, and to store a trend of the anemia status over time.

2. The medical system of claim 1, further comprising a heart failure diagnostics module configured to detect an onset of heart failure decompensation based on the anemia status trend.

3. The medical system of claim 1, wherein the implantable circuitry and the anemia module are incorporated in an implantable cardiac therapy device, the cardiac therapy device further comprising a cardiac therapy controller configured to control a cardiac pacing therapy based on the anemia status trend.

4. The medical system of claim 1, wherein the anemia module is further configured to generate an alert signal based on the anemia status trend.

5. The medical system of claim 1, wherein the anemia module is further configured to evaluate thromboembolism risk and to generate an alert signal based on the thromboembolism risk.

6. An implantable medical system, comprising:
an implantable sensor configured to sense blood viscosity;
an anemia module configured to compare the blood viscosity to one or more thresholds respectively associated with one or more hematocrit levels and to determine an anemia status of a patient based on comparison of the blood viscosity to the one or more thresholds; and
a therapy module configured to deliver therapy to the patient based on the anemia status or blood viscosity.

7. The medical system of claim 6, wherein:
the anemia module is configured to evaluate thromboembolism risk; and
the therapy module is configured to deliver therapy to the patient based on the thromboembolism risk.

8. The medical system of claim 6, wherein the therapy module delivers a drug.

9. The medical system of claim 6, wherein the therapy module comprises an electrical stimulator configured to deliver electrical stimulation therapy to one or both kidneys.

10. The medical system of claim 9, wherein the therapy module is configured to provide cardiac resynchronization pacing for heart failure.

11. The medical system of claim 6, wherein the anemia module is configured to detect an onset of heart failure decompensation based on the anemia status and to generate an alert signal in response to detection of the onset of heart failure decompensation.

12. The medical system of claim 6, wherein the anemia module is configured to generate an alert signal based on the anemia status.

13. The medical system of claim 6, wherein the therapy module is configured to electrically stimulate a hypothalamus.

14. The medical system of claim 6, wherein the implantable sensor comprises an acoustic sensor.

15. An implantable medical system, comprising:
an implantable sensor configured to sense blood viscosity;
an anemia module configured to compare the blood viscosity to one or more thresholds respectively associated with one or more hematocrit levels and to determine an anemia status of a patient based on comparison of the blood viscosity to the one or more thresholds; and
a therapy module configured to control an electrical stimulation therapy delivered to one or both kidneys or a hypothalamus of the patient based at least in part on the anemia status.

16. The medical system of claim 15, wherein:
the anemia module is configured to trend the anemia status of the patient over time; and
the therapy module is configured to control the electrical stimulation therapy based on a rate of change in the anemia status trend.

17. The medical system of claim 15, wherein the anemia module is configured to trend the anemia status over time and monitor a progression of heart failure based on the anemia status trend.

18. The medical device of claim 17, wherein the anemia module is configured to modify a heart failure therapy based on the anemia status trend.

19. The medical device of claim 17, wherein the anemia module is configured to adjust biventricular pacing based on the anemia status trend.

20. The medical device of claim 15, wherein the anemia module is configured to detect hemodilutional anemia and to detect an onset of a heart failure decompensation event based on the detection of the hemodilutional anemia.

21. An implantable medical system, comprising:

an implantable sensor configured to sense blood viscosity;

an anemia module configured to compare the blood viscosity to one or more thresholds respectively associated with one or more hematocrit levels and to determine an anemia status of a patient based on comparison of the blood viscosity to the one or more thresholds, and wherein the anemia module is further configured to detect hemodilutional anemia and to detect an onset of a heart failure decompensation event based on the detection of the hemodilutional anemia; and a therapy module configured to control an electrical stimulation therapy delivered to one or both kidneys or a hypothalamus of the patient based at least in part on the anemia status.

* * * * *